US010201276B2

United States Patent
Neal et al.

(10) Patent No.: US 10,201,276 B2
(45) Date of Patent: Feb. 12, 2019

(54) OPTICAL MEASUREMENT SYSTEMS AND PROCESSES WITH WAVEFRONT ABERROMETER HAVING VARIABLE FOCAL LENGTH LENS

(71) Applicant: AMO WaveFront Sciences, LLC, Santa Ana, CA (US)

(72) Inventors: Daniel R. Neal, Tijeras, NM (US); Richard J. Copland, Albuquerque, NM (US)

(73) Assignee: AMO WaveFront Sciences, LLC, Santa Ana, CA (US)

(*) Notice: Subject to any disclaimer, the term of this patent is extended or adjusted under 35 U.S.C. 154(b) by 0 days.

(21) Appl. No.: 15/697,297

(22) Filed: Sep. 6, 2017

(65) Prior Publication Data

US 2018/0064338 A1     Mar. 8, 2018

Related U.S. Application Data

(60) Provisional application No. 62/384,090, filed on Sep. 6, 2016.

(51) Int. Cl.
*A61B 3/15*     (2006.01)
*A61B 3/00*     (2006.01)
(Continued)

(52) U.S. Cl.
CPC ............ *A61B 3/158* (2013.01); *A61B 3/0025* (2013.01); *A61B 3/101* (2013.01); *A61B 3/102* (2013.01);
(Continued)

(58) Field of Classification Search
CPC ..... A61B 3/107; A61B 3/0025; A61B 3/1015; A61B 3/14; A61F 2009/00872;
(Continued)

(56) References Cited

U.S. PATENT DOCUMENTS 5,777,719 A    7/1998   Williams et al.
6,550,917 B1   4/2003   Neal et al.
(Continued)

FOREIGN PATENT DOCUMENTS

EP     2656781 A1    10/2013

OTHER PUBLICATIONS

International Search Report and Written Opinion for Application No. PCT/US2017/050352, dated Dec. 14, 2017, 11 pages.
(Continued)

*Primary Examiner* — Mohammed Hasan
(74) *Attorney, Agent, or Firm* — Johnson & Johnson Surgical Vision, Inc.

(57) ABSTRACT

An optical measurement system: passes a probe light beam through a variable focal length lens to the retina of an eye, and returns light from the retina through the variable focal length lens to a wavefront sensor; adjusts the focal length of the variable focal length lens to provide a desired characteristic to at least one of: the probe light beam, and the light returned by the retina to the wavefront sensor; passes a calibration light through the variable focal length lens to the wavefront sensor while the variable focal length lens is at the adjusted focal length to ascertain the adjusted focal length; and makes a wavefront measurement of the eye from the light returned from the retina of the eye through the variable focal length lens to the wavefront sensor, and from the adjusted focal length ascertained from the calibration light received by the wavefront sensor.

24 Claims, 11 Drawing Sheets

(51) Int. Cl.
*A61B 3/10* (2006.01)
*A61B 3/103* (2006.01)
*A61F 9/008* (2006.01)
*A61B 3/107* (2006.01)
*A61B 34/10* (2016.01)

(52) U.S. Cl.
CPC .............. *A61B 3/103* (2013.01); *A61B 3/107* (2013.01); *A61B 3/1015* (2013.01); *A61F 9/00804* (2013.01); *A61B 2034/102* (2016.02); *A61F 2009/0088* (2013.01); *A61F 2009/00872* (2013.01); *A61F 2009/00882* (2013.01)

(58) Field of Classification Search
CPC .................. A61F 9/008; A61F 9/00804; A61F 2009/00882; A61F 2/1613; A61F 2009/00848; A61F 2009/0088; A61F 2009/00895; A61F 9/00827

USPC ......................................................... 351/212
See application file for complete search history.

(56) References Cited

U.S. PATENT DOCUMENTS

| | | |
|---|---|---|
| 7,980,699 B2 | 7/2011 | Neal et al. |
| 2002/0159030 A1* | 10/2002 | Frey .................... A61B 3/1015 351/212 |
| 2003/0071969 A1 | 4/2003 | Levine et al. |
| 2018/0242840 A1* | 8/2018 | Copland .............. A61B 3/1005 |

OTHER PUBLICATIONS

Mejía-Barbosa Y., et al., "Object Surface for Applying a Modified Hartmann Test to Measure Corneal Topography," Applied Optics, Nov. 1, 2001, vol. 40 (31), pp. 5778-57786.

* cited by examiner

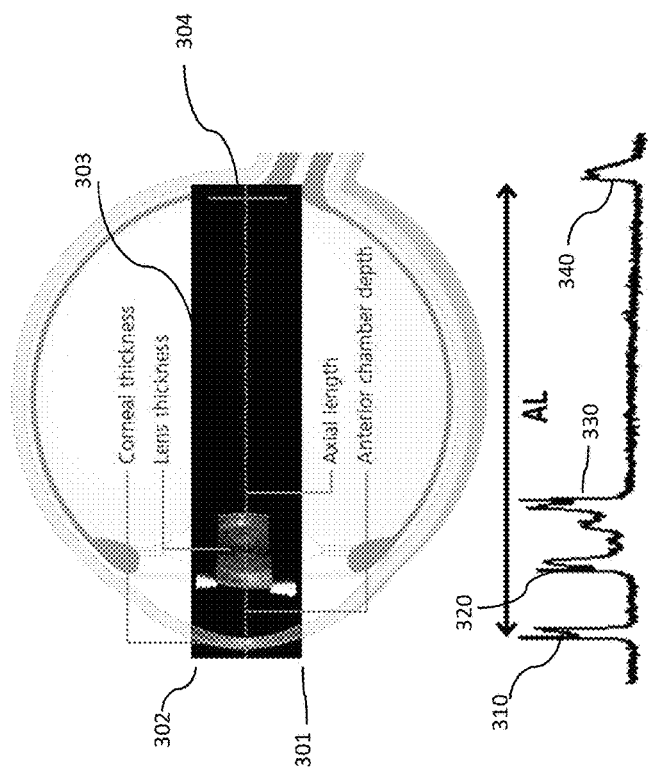
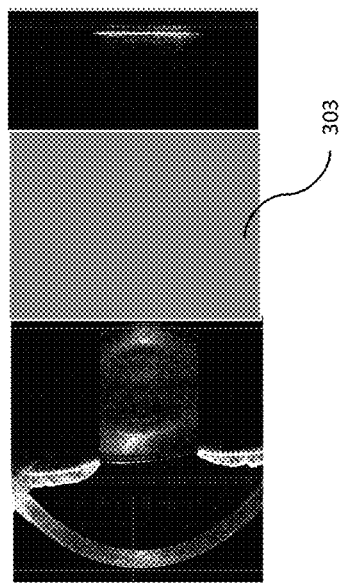
FIG. 8A
FIG. 8B
FIG. 8C

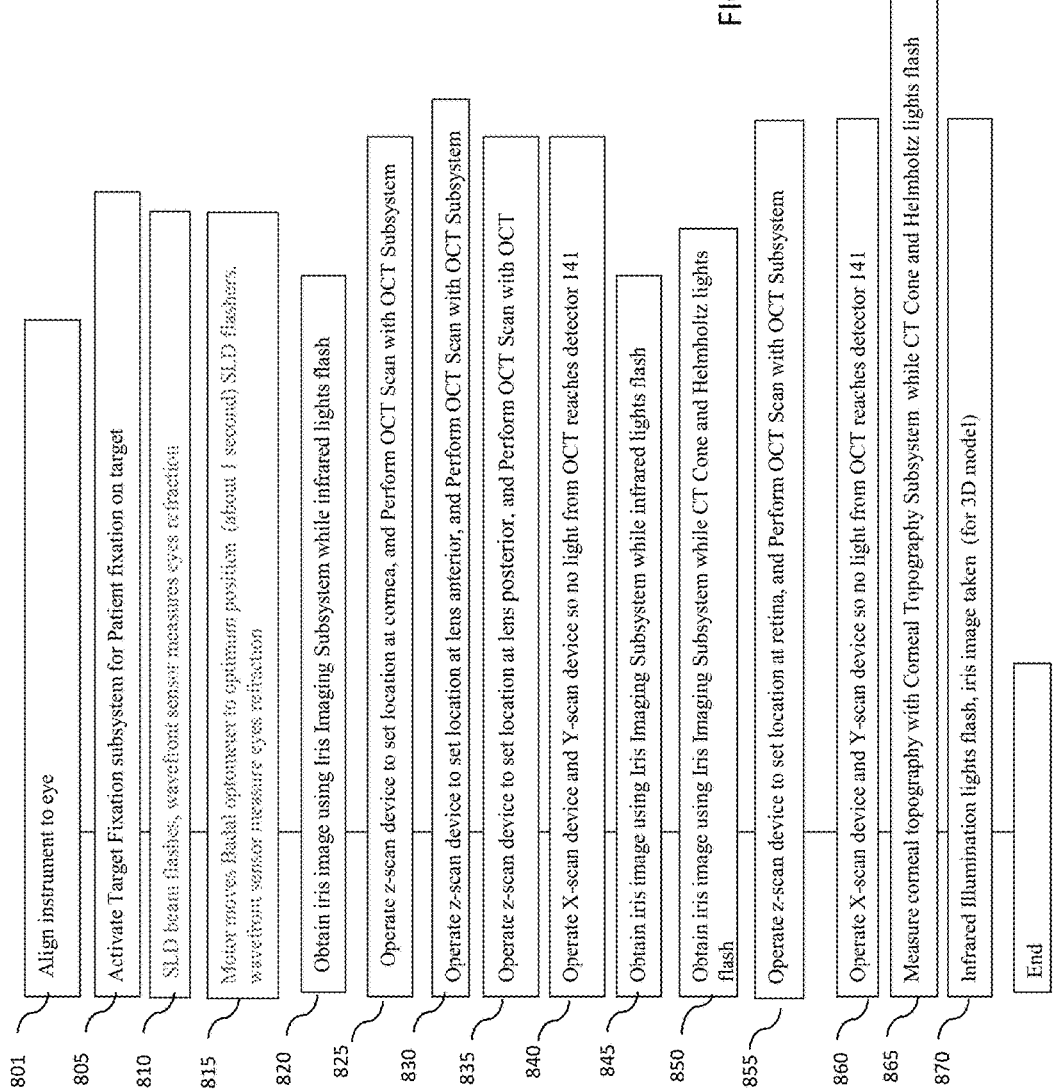

OPTICAL MEASUREMENT SYSTEMS AND PROCESSES WITH WAVEFRONT ABERROMETER HAVING VARIABLE FOCAL LENGTH LENS

RELATED APPLICATIONS

This application claims priority to, and the benefit of, under 35 U.S.C. § 119(e) of U.S. Provisional Appl. No. 62/384,090, filed Sep. 6, 2016, which is incorporated herein by reference in its entirety.

TECHNICAL FIELD

Embodiments of this invention pertain to optical measurement equipment, and more particularly, to optical measurement systems and processes which include components and methods for making wavefront aberrometry measurements of a subject's using a wavefront aberrometer having a variable focal length lens.

BACKGROUND

Aberrometers measure the refraction of a subject's eye using infrared light.

U.S. Pat. No. 6,550,917, which is incorporated herein by reference, describes an instrument which provides an adjustable telescope in the forward path from the light source to the eye and in the return path from the eye to the wavefront sensor. The adjustable telescope employs a moving stage to move one lens of the telescope with respect to the other, and a feedback arrangement whereby data from the wavefront sensor is employed to control a motor for the moving stage to move the stage to the desired location where the wavefront sensor sees collimated return light from the eye. The moving stage may be a common linear travel stage with stepper (or servo) motor drives and a position encoder. The position of the moving stage may be calibrated so the stage position corresponds to the refractive power of the eye being measured. U.S. Pat. No. 6,550,917 also discloses with respect to FIG. 7 that a variable local length lens may be employed in lieu of a moving stage in order to correct lower order aberrations in the returned light from the eye which is provided to the wavefront sensor However, U.S. Pat. No. 6,550,917 does not disclose any technique for determining the current focal length of the variable focal length lens when it is employed for measuring a subject's eye. This information is needed to process the wavefront sensor data to determine the aberrations of the subject's eye. Ideally the variable focal lens would operate in a manner such that a control input signal would result in a repeatable setting. However, commercially available devices demonstrate poor repeatability, particularly when the temperature of the operating environment is not stable. Such a situation may occur, for instance, when an instrument is turned on and then heat generated by components in the case causes the internal temperature of the instrument to rise, or when an instrument is built in an open air environment which naturally keeps the instrument cool, but in actual usage a cover is installed that traps heat so the usage conditions are different.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIG. 8A illustrates a preferred scanning region for the OCT subsystem according to many embodiments of the present invention.

FIG. 8B shows a representative graph of an intensity of an OCT signal of an OCT subsystem according to many embodiments as a function of depth along the axis defining the axial length of the eye.

FIG. 8C shows a cross-section of an eye obtained by an optical measurement system of the present invention using an OCT subsystem according to the present invention

FIG. 10 is a flowchart of an example embodiment of a method for measuring one or more characteristics of an eye, including wavefront aberrometry, corneal topography and OCT measurements at various locations with the eye along the axial length of the eye.

DETAILED DESCRIPTION

Exemplary embodiments of optical measurement systems and methods for measuring aberrations of an eye to illustrate various aspects and advantages of these devices and methods are described below. However, it should be understood that the principles involved in these devices and methods can be employed in a variety of other contexts, and therefore the novel devices and method disclosed and claimed here should not be construed as being limited to the example embodiments described below.

Figure 1:
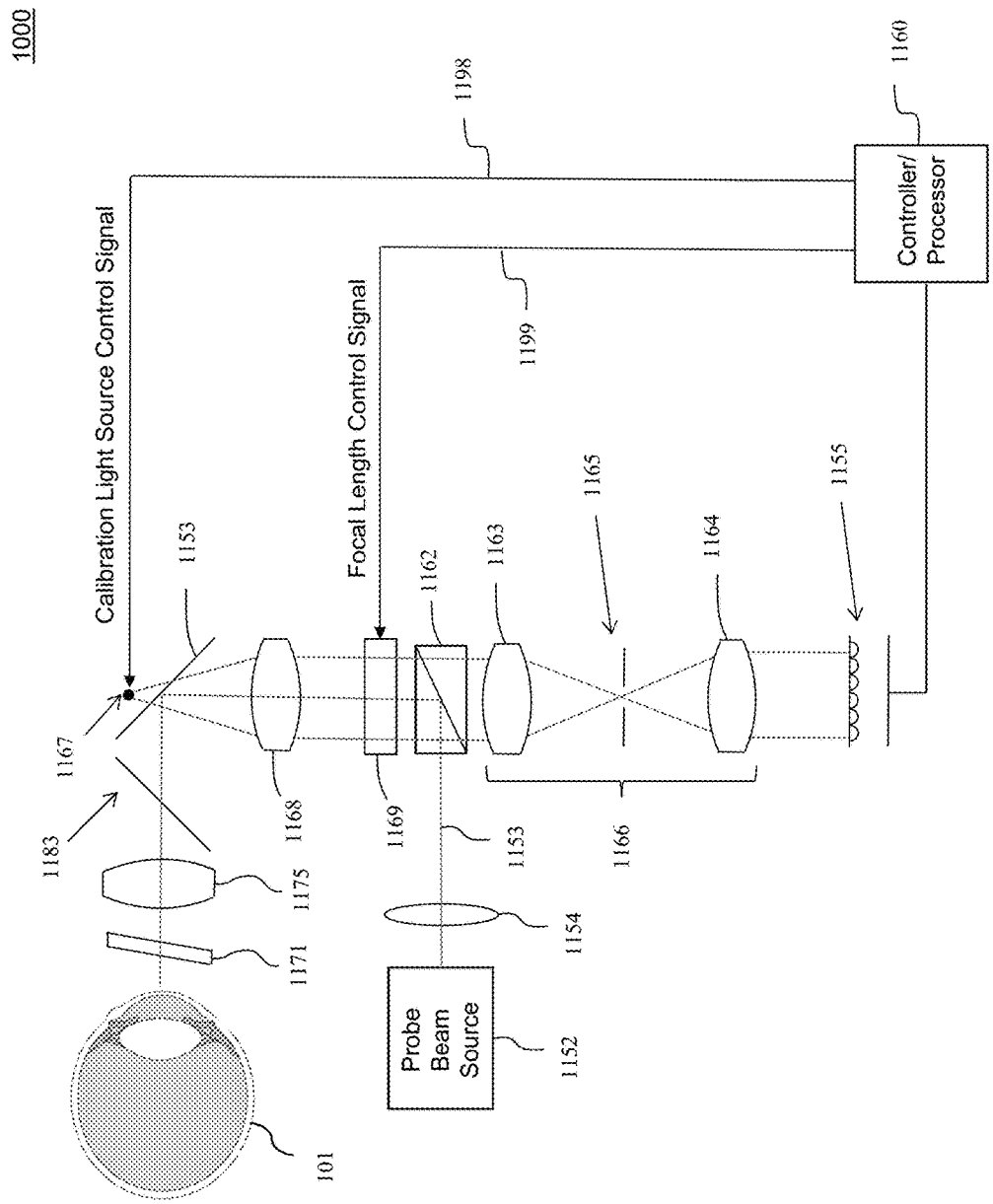
FIG. 1 illustrates an example embodiment of a wavefront aberrometer which employs an adjustable focal length lens.

FIG. 1 illustrates an example embodiment of a wavefront aberrometer 1000 for measuring one or more characteristics of an eye 101. Wavefront aberrometer 1000 includes a probe light beam source 1152, an optical element 1154, a wavefront sensor 1155, a polarizing beamsplitter 1162, an optical imaging system 1166, a variable focal length lens 1169, an optical element 1168, a beamsplitter 1167, a beamsplitter 1183, optical element 1175, and a quarter wave ($\lambda/2$) polarizer plate 1171, and a controller/processor 1160.

Probe light beam source 1152 may comprise a laser, a laser diode, LED, or a super-luminescent diode (SLD), which may be connected to an optical fiber. For safety reasons, light source 1152 may be a pulsed light source, may be limited to a small power level, and may be outside the normal visual detection range, e.g. infrared.

Here, wavefront sensor 1155 is a Shack-Hartmann wavefront sensor. The operation of a Shack-Hartmann wavefront sensor in a wavefront aberrometer such as wavefront aberrometer 1000 may be understood with reference to U.S. Pat. No. 6,550,917, and will not be repeated here. In other embodiments, a shearing interferometer or a Moiré deflectometer may be employed as a wavefront sensor.

Optical imaging system 1166 includes a telescope comprising a pair of lenses 1163 and 1164, and a dynamic range limiting aperture 1165, for example in a optical screening structure.

Variable focal length lens 1169 may be a liquid filled lens whose focal length or magnification may be adjusted in response to a focal length control signal (e.g., an electrical signal) 1199 which may be provided from controller/processor 1160. Other embodiments of variable focal length lens 1169 are also contemplated, such as an electrostatic membrane lens, or one or more optomechanical elements.

Controller 1160 controls the operation of wavefront aberrometer 1000 and can receive image data from wavefront sensor 1155 and process the image data to control the focal length or magnification of variable focal length lens 1169 and to measure the refraction of eye 101, including high order aberrations. Controller 1160 may include any suitable components, such as one or more processor, one or more field-programmable gate array (FPGA), and one or more memory storage devices.

As noted above, in some embodiments, probe light beam source 1152 may be coupled to an optical fiber, which may be a polarization maintaining optical fiber. The light output by probe light beam source 1152 may be provided to optical element optical element 1154, which may be a collimating lens, to generate a probe light beam 1153. The use of an optical fiber to deliver light from the light source 1152 may simplify collimating lens 1154, since the fiber exit mode acts as a diffraction-limited point source. In that case, collimating lens 1154 may be rigidly mounted to the optical fiber. Collimated probe light beam 1153 may then be truncated to a desired size by an aperture. If needed, a polarizer may be provided for polarizing collimated probe light beam 1153.

Alternatively, light source 1152 may be provided alone, i.e., without the use of an optical fiber. The light from light source 1152 itself may be then collimated by collimating lens 1154. While light sources used for ophthalmic measurement typically have a high degree of astigmatism, by using only a portion of the beam, e.g., 10-25%, typically from the center of the beam, the wavefront error over the beam is small enough that the beam size is substantially stable over the distance traversed in wavefront aberrometer 1000. In other words, even though the beam is still astigmatic, the beam shape does not change while traversing the ophthalmic measurement system due to this astigmatism, so the astigmatism does not influence the measurement. Probe light beam 1153 may be polarized as required.

As an additional safety measure, a small portion of the probe light beam incident on beam splitter 1183 may be transmitted to a lens (not shown) which focuses the light onto a power monitor. The output of this power monitor may be used to shut down the system if the power exceeds the safety limits of wavefront aberrometer 1000 or to alter the power supplied to light source 1152 to reduce the power output by light source 1152 in a known manner Variable focal length lens 1169 comprises a pre-correction system which compensates the probe light beam 1153 to be injected into eye 101 for aberrations in eye 101 by adding a desired pre-correction for the injected probe light beam 1153 by adding defocus that just compensates for the spherical equivalent defocus of eye 101 which is being measured.

In operation, probe light beam 1153 from light source 1162 is directed by beam splitter 1162, via variable focal length lens 1169, optical element (e.g., lens) 1168, beamsplitters 1167 and 1183, optical element (e.g., lens) 1175, and quarter wave plate 1171, to eye 101 under measurement. The injected beam is focused by the lens of eye 101 to a focal spot on the retina of eye 101. Light from this focal spot is scattered or reflected by the retina and returned to wavefront aberrometer 1000 via the cornea of the eye.

The returned light from the retina is collected by the cornea and lens of eye 101 and is approximately collimated. Quarter wave plate 1171, optical element (e.g., lens) 1175, beamsplitters 1167 and 1183, optical element (e.g., lens) 1168 direct the returned light from eye 101 back to variable focal length lens 1169. Imaging system 1166 images the light from adjustable focal length lens 1169 onto wavefront sensor 1155. The same adjusted focal length for adjustable focal length lens 1169 which corrects for the defocus aberrations of eye 101, also ensures that the returned light arrives at a wavefront sensor 1155 collimated to within the dynamic range of wavefront sensor 1155. Dynamic range limiting aperture 1165 blocks any rays outside the angular dynamic range of wavefront sensor 1155 so that no mixing or measurement confusion occurs. When the wavefront sensor 1155 is a Shack-Hartmann sensor, the focal spots cannot collide, interfere or cause confusion with adjacent focal spots. In an alternative embodiment, the relative optical positions of beam splitter 1162 and variable focal length lens 1169 may be reversed such that the probe light beam 1153 does not pass through variable focal length lens 1169, and only the light returned from eye 101 to wavefront sensor 1155 passes through variable focal length lens 1169.

Beneficially, controller/processor 1160 controls or adjusts the focal length or magnification of adjustable focal length lens 1169 to have an adjusted focal length to provide a desired characteristic to at least one of: probe light beam 1153 injected into eye 101, or the light received by wavefront sensor 1155 from the retina of eye 101.

The proper or desired adjusted focal length for adjustable focal length lens 1169 may be determined in a number of ways. In some embodiments, an additional beam splitter may be provided in an optical path between imaging system 1166 and wavefront sensor, and a focusing lens and a detector may be used to create an image of the light incident upon the retina. In that case, the proper or desired adjusted focal length may determined by minimizing the waveform error at the wavefront sensor. In practice, this may correspond to minimizing the spot size on the back of the retina, performed by comparing the spot sizes from different focal length values for adjustable focal length lens 1169. Beneficially eye 101 is arranged to be one focal length of objective lens 1168, and wavefront sensor 1155 is arranged to be at the conjugate image plane to eye 101.

Meanwhile, controller/processor 1160 receives image data ("first image data") from wavefront sensor 1155 produced in response to the light returned from the retina of eye 101, and processes the first image data to determine the refraction of eye 101.

However, to correctly determine the refraction of eye 101 from the image data produced by wavefront sensor 1155, controller/processor 1160 needs to know the adjusted focal length to which adjustable focal length lens 1169 was set when the image data was captured.

To address this need, wavefront aberrometer 1000 also includes a switchable calibration light source 1167 which is configured, when turned on, to provide a calibration light to wavefront sensor 1155 via adjustable focal length lens 1169. In some embodiments, switchable calibration light source 1167 may comprise a switchable LED which passes the calibration light through a pinhole. In some embodiments, switchable calibration light source 1167 may be switched ON and OFF in response to a calibration light source control signal (e.g., an electrical signal) 1198 from controller/processor 1160. In some embodiments, the wavelength of switchable calibration light source 1167 may be different than the wavelength of the probe light beam used for the wavefront measurements of eye 101, so long as the focal length or magnification of variable focal length lens 1169 is the same at both wavelengths, or at a minimum has a known relationship between the two wavelengths which relationship may be provided to controller/processor 1160 (e.g., an offset value stored in memory).

By processing the image data ("second image data") produced by wavefront sensor 1155 from the locations of the spots produced on the detector of wavefront sensor 1155 in response to the calibration light from calibration light source 1167, using standard signal processing techniques, controller/processor 1160 may determine the adjusted focal length of adjustable focal length lens 1169.

Accordingly, controller/processor 1160 may adjust variable focal length lens 1169 to a desired or proper adjusted focal length while probe light beam 1153 is turned on, as explained above, and while switchable calibration light source 1167 may be turned OFF. Then, either before or after (or both, for redundancy) wavefront sensor 1155 produces the first image data in response to the light returned from the retina, and while variable focal length lens 1169 is still set at the desired or proper adjusted focal length, switchable calibration light source is turned ON and wavefront sensor 1155 outputs the second image data produced by wavefront sensor 1155 from the locations of the spots produced on the detector of wavefront sensor 1155 in response to the calibration light, which may be processed by controller/processor 1160 using standard signal processing techniques to determine the adjusted focal length of adjustable focal length lens 1169.

Controller/processor 1160 may then measure a parameter (e.g., determine a portion of the refraction or aberrations) of eye 101 from the first image data produced while variable focal length lens 1169 has the adjusted focal length, and from the value of the adjusted focal length itself ascertained from the second image data. The optical power of the adjustable focal length lens is added to the optical power determined from the first image to determine the total refractive power of the eye. Similarly any astigmatism or wavefront aberrations of the variable focal length lens determined from the second image data may be subtracted from any astigmatism or wavefront aberrations measured from the first image data to determine the total astigmatism and aberrations of the eye. The simple linear relationship is a result of the adjustable focal length lens being located at a position that is conjugate to the pupil of the eye. This is a consequence of the fact that eyes are characterized by the power needed to correct them. That is, a myope, who has an eye that is too long for his lens power (or too strong lens power for his eye length) actually has a positive optical power of his lens (too strong). To correct you need a negative lens to reduce some of this optical power to get the light to focus at the right place. Thus a myope has a negative refraction value.

In some embodiments, the control of variable focal length lens 1169 by focal length control signal 1199 may be sufficiently linear as long as the temperature is constant, such that a measurement of the adjusted focal length of variable focal length lens 1169 is not required to be repeated for each separate wavefront measurement of eye 101, in which case the measurement of the adjusted focal length of variable focal length lens 1169 may only be performed periodically.

The system in FIG. 1 has a single light source providing the calibration light signal to the wavefront sensor. In the arrangement shown, when the adjust focal length is adjusted for measuring strongly myopic or hyperopic eyes, the vergence of the light rays may exceed the range that that the wavefront sensor is normally set to analyze. Then the system would not have the information needed to calculate an accurate refraction. One solution is that the system may use flip-in auxiliary lenses of known power near the light source to make the light near collimated on the wavefront sensor. Another solution is that the system may use special reference files for analyzing those cases of extreme vergence. With extreme vergence cases, the light beam that passes through range limiting aperture 1166 will be clipped so a reduced beam diameter appears on the wavefront sensor. If it is only desired to know the base power of the adjustable focal length lens, the reduced diameter beam will still have enough information. But if it is desired to sample the entire lens, the range limiting aperture diameter needs to be increased during the lens measurement. One simple method of accomplishing this is to locate the regular aperture on a motorized swing out arm. When the normal aperture is flipped out, a larger aperture behind it is exposed.

FIG. 1 shows the probe beam illumination passing through the adjustable lens. However for some commercially available lenses this is a poor choice because the back reflections from an internal membrane in the lens may reach the wavefront sensor and ruin the measurement. For those particular kinds of lenses, the probe beam may be introduced into the eye from another optical path. If the probe beam has a large diameter, another adjustable element may be required to focus it on the retina for each eye. Alternatively, the probe beam diameter may be made very small so that a lens for focusing the probe beam on the retina is not necessary.

Figure 2:
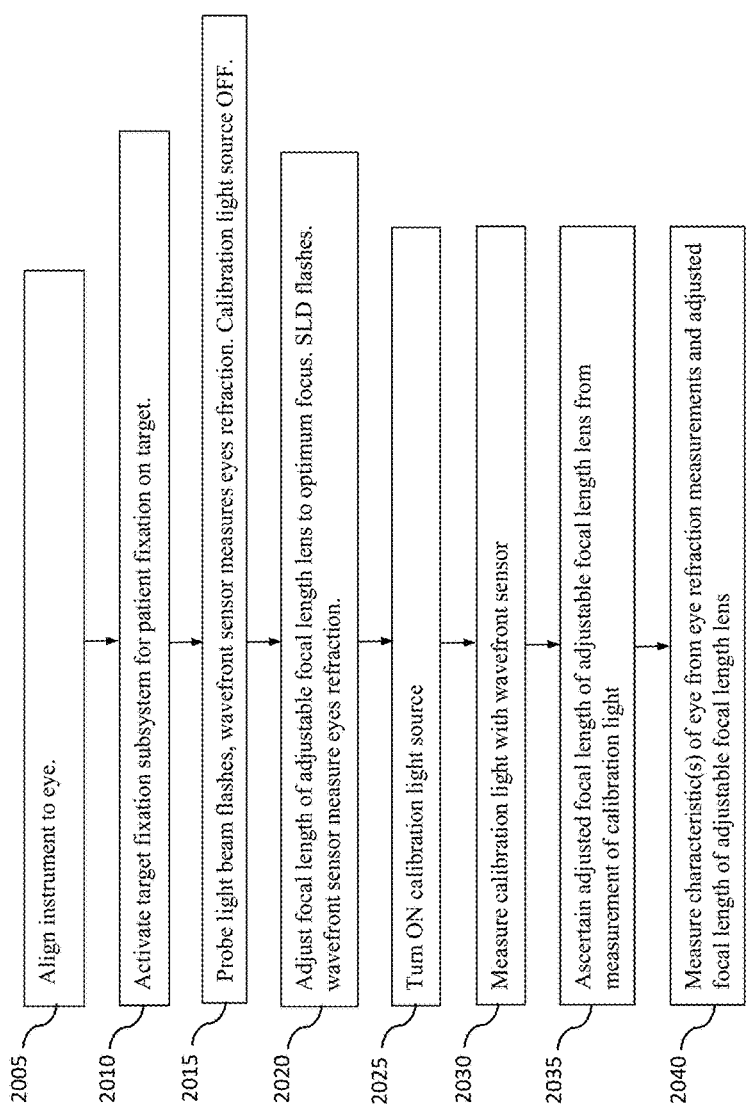
FIG. 2 is a flowchart of an example embodiment of a method of measuring one or more characteristics of an eye with a wavefront aberromoter.

FIG. 2 is a flowchart of an example embodiment of a method 2000 of measuring one or more characteristics of an eye with a wavefront aberromoter such as wavefront aberrometer 1000.

An operation 2005 includes aligning the measurement instrument, including the wavefront aberrometer, to the eye to be measured.

An operation 2010 includes activating a target fixation subsystem for patient fixation on target.

An operation 2015 includes flashing a probe light beam, and the wavefront sensor measures the eye's refraction. In operation 2015, the calibration light source is OFF.

An operation 2020 includes adjusting the focal length of the adjustable focal length lens to optimum focus. Then the probe light beam is flashed again, and the wavefront sensor once again measures the eye's refraction. Here, again, the calibration light source is OFF.

An operation 2025 includes turning ON the calibration light source.

An operation 2030 includes measuring the calibration light with the wavefront sensor.

An operation 2035 includes ascertaining the adjusted focal length of the adjustable focal length lens from the measurement of the calibration light by the wavefront sensor.

An operation 2040 includes measuring one or more characteristics of the eye from the eye refraction measurements of the wavefront sensor, and the value of the adjusted focal length of the adjustable focal length lens.

The principles of wavefront aberrometer 1000 including a variable focal length lens and an arrangement and method for ascertaining the value of the adjusted focal length of the adjustable focal length lens, as described above, may be applied to an optical measurement instrument which includes additional functionality, such as the ability to measure corneal topography and/or to make optical coherence tomography (OCT) measurements of interior structures of the eye. Embodiments of such an optical measurement instrument, and methods of operation thereof, will now be described.

Figure 3C:
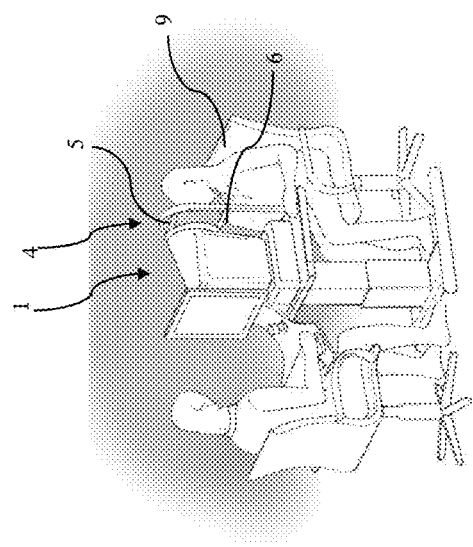
FIG. 3C illustrates a side perspective view showing an optical measurement system according to many embodiments.
Figure 3A:
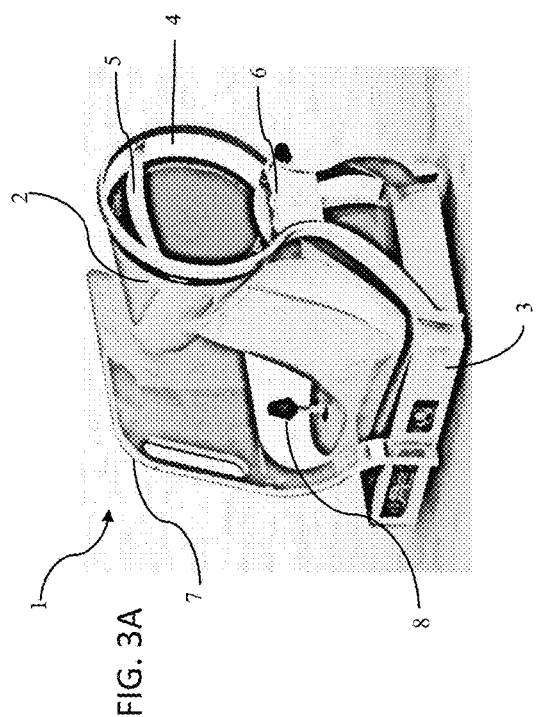
FIG. 3A illustrates a front perspective view showing an optical measurement system according to many embodiments.
Figure 3B:
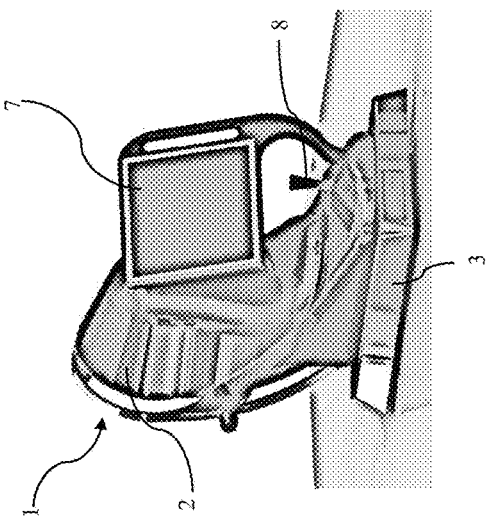
FIG. 3B illustrates a rear perspective view showing an optical measurement system according to many embodiments.

As shown in FIGS. 3A-3C, an optical measurement system 1, according to many embodiments, is operable to provide for a plurality of measurements of the human eye, including wavefront aberrometry measurements, corneal topography measurements, and optical coherence tomography measurements to measure characteristics of the cornea, the lens capsule, the lens and the retina. Optical measurement system 1 includes a main unit 2 which comprises a base 3 and includes many primary subsystems of many embodiments of the system 1. For example, externally visible subsystems include a touch-screen display control panel 7, a patient interface assembly 4 and a joystick 8.

Patient interface 4 may include one or more structures configured to hold a patient's head in a stable, immobile and comfortable position during the diagnostic measurements while also maintaining the eye of the patient in a suitable alignment with the diagnostic system. In a particularly preferred embodiment, the eye of the patient remains in substantially the same position relative to the diagnostic system for all diagnostic and imaging measurements performed by the system 1.

In one embodiment the patient interface includes a chin support 6 and/or a forehead rest 4 configured to hold the head of the patient in a single, uniform position suitably aligned with respect to the system 1 throughout the diagnostic measurement. As shown in FIG. 3C, the optical measurement system 1 may be disposed so that the patient may be seated in a patient chair 9. Patient chair 9 can be configured to be adjusted and oriented in three axes (x, y, and z) so that the patent's head can be at a suitable height and lateral position for placement on the patient interface.

In many embodiments, the system 1 may include external communication connections. For example, the system 1 can include a network connection (e.g., an RJ45 network connection) for connecting the system 1 to a network. The network connection can be used to enable network printing of diagnostic reports, remote access to view patient diagnostic reports, and remote access to perform system diagnostics. The system 1 can include a video output port (e.g., HDMI) that can be used to output video of diagnostic measurements performed by the system 2. The output video can be displayed on an external monitor for, for example, viewing by physicians or users. The output video can also be recorded for, for example, archival purposes. The system 2 can include one or more data output ports (e.g., USB) to enable export of patient diagnostic reports to, for example, a data storage device or a computer readable medium, for example a non-volatile computer readable medium, coupled to a laser cataract surgery device for use of the diagnostic measurements in conducting laser cataract surgeries. The diagnostic reports stored on the data storage device or computer readable medium can then be accessed at a later time for any suitable purpose such as, for example, printing from an external computer in the case where the user without access to network based printing or for use during cataract surgery, including laser cataract surgery.

Figure 4:
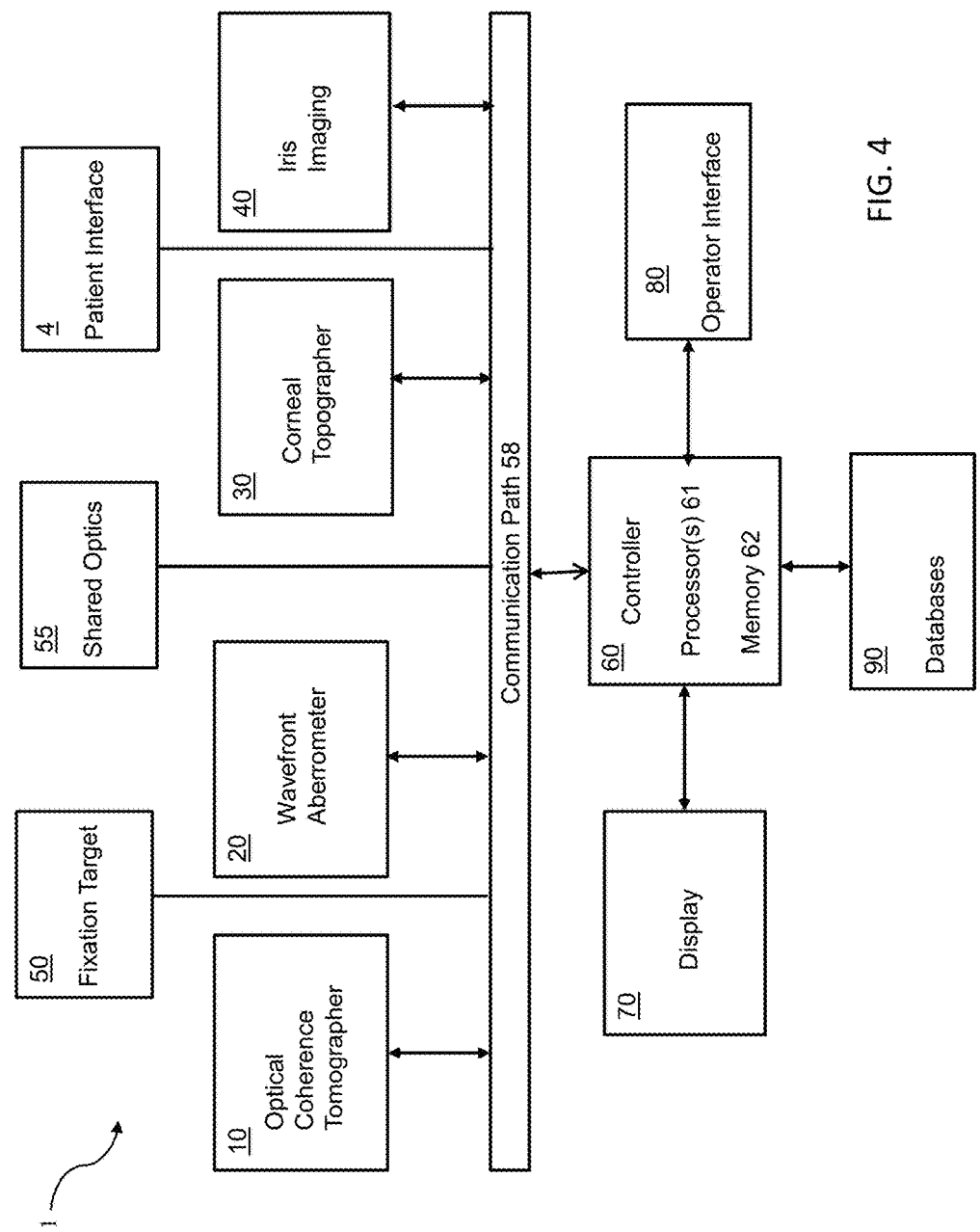
FIG. 4 is a block diagram of a system including an optical measurement instrument, and a position of an eye relative to the system according to one or more embodiments described herein which may be used by the optical measurement.

FIG. 4 is a block diagram of a system including an optical measurement instrument 1 according to one or more embodiments described herein. Optical measurement instrument 1 includes: an optical coherence tomographer (OCT) subsystem 10, a wavefront aberrometer subsystem 20, and a corneal topographer subsystem 30 for measuring one or more characteristics of a subject's eye. Optical measurement instrument 1 may further include an iris imaging subsystem 40, a fixation target subsystem 50, a controller 60, including one or more processor(s) 61 and memory 62, a display 70 and an operator interface 80. Optical measurement instrument 1 further includes a patient interface 4 for a subject to present his or her eye for measurement by optical measurement instrument 1.

The optical coherence tomography subsystem 10 is configured to measure the spatial disposition (e.g., three-dimensional coordinates such as X, Y, and Z of points on boundaries) of eye structures in three dimensions. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, the limbus and/or the retina. The spatial disposition of the structures of interest and/or of suitable matching geometric modeling such as surfaces and curves can be generated and/or used by the controller for a number of purposes, including, in some embodiment to program and control a subsequent laser-assisted surgical procedure. The spatial disposition of the structures of interest and/or of suitable matching geometric modeling can also be used to determine a wide variety of parameters.

As a non-limiting example, the system 1 can be configured to use a swept source OCT imaging system employing wavelengths of around 1060 nm with an 8 mm scan depth. The spatial disposition of the eye structures using optical coherence tomography should generally be measured while the patient is engaged with patient interface 4. The OCT scan depth may be between 8 and 50 mm, and the scan depth may be greater than about 24 mm or even 30 mm to achieve a full eyescan depth. The swept source wavelengths can be centered at wavelengths from 840 nm to 1310 nm.

Optical coherence tomographer subsystem 10 is only one example of an eye structure imaging subsystem which may be employed in optical measurement instrument 1. In other embodiments, a different eye structure imaging subsystem may be employed, for example a Scheimplug Imager, a fluorescence imager, a structured lighting imager, a wavefront tomographer, an ultrasound imager and a plenoptic imager.

The wavefront aberrometer subsystem 20 is configured to measure ocular aberrations, which may include low and high order aberrations, by measuring the wavefront emerging from the eye by, for example a Shack Hartman sensor.

The corneal topographer subsystem 30 may apply any number of modalities to measure the shape of the cornea including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack measurement of the eye, a Scheimpflug image topography of the eye, a confocal tomography of the eye, a Helmholtz source topographer, or a low coherence reflectometry of the eye. The shape of the cornea should generally be measured while the patient is engaged with patient interface 4.

Fixation target system 50 is configured to control the patient's accommodation, because it is often desired to measure the refraction and wavefront aberrations when eye 101 is focused at its far point Images captured by the corneal topographer subsystem 10, the wavefront aberrometer 20, the optical coherence tomographer subsystem 30 or the camera 40 may be displayed with a display of the operator interface 80 of the optical measurement system 2 or the display 70 of the optical measurement system, respectively. The operator interface may also be used to modify, distort, or transform any of the displayed images.

The shared optics 55 provide a common propagation path that is disposed between the patient interface 4 and each of the optical coherence tomographer (OCT) subsystem 10, the wavefront aberrometer subsystem 20, the corneal topographer subsystem 30, and in some embodiments, the camera 40, and the fixation target 50. In many embodiments, the shared optics 55 may comprise a number of optical elements, including mirrors, lenses and beam combiners to receive the emission from the respective subsystem to the patient's eye and, in some cases, to redirect the emission from a patient's eye along the common propagation path to an appropriate director.

The controller 60 controls the operation of the optical measurement instrument 1 and can receive input from any of the optical coherence tomographer (OCT) subsystem 10, the wavefront aberrometer subsystem 20, the corneal topographer subsystem 30 for measuring one or more characteristics of a subject's eye, the camera 40, the fixation target 50, the display 70 and the operator interface 80 via the communication paths 58. The controller 60 can include any suitable components, such as one or more processor, one or more field-programmable gate array (FPGA), and one or more memory storage devices. In many embodiments, the controller 60 controls the display 70 to provide for user control over the laser eye surgery procedure for pre-cataract procedure planning according to user specified treatment parameters as well as to provide user control over the laser eye surgery procedure. The communication paths 58 can be implemented in any suitable configuration, including any suitable shared or dedicated communication paths between the controller 60 and the respective system components.

The operator interface 80 can include any suitable user input device suitable to provide user input to the controller 60. For example, the user interface devices 80 can include devices such as joystick 8, a keyboard or a touchscreen display 70.

Figure 5A:
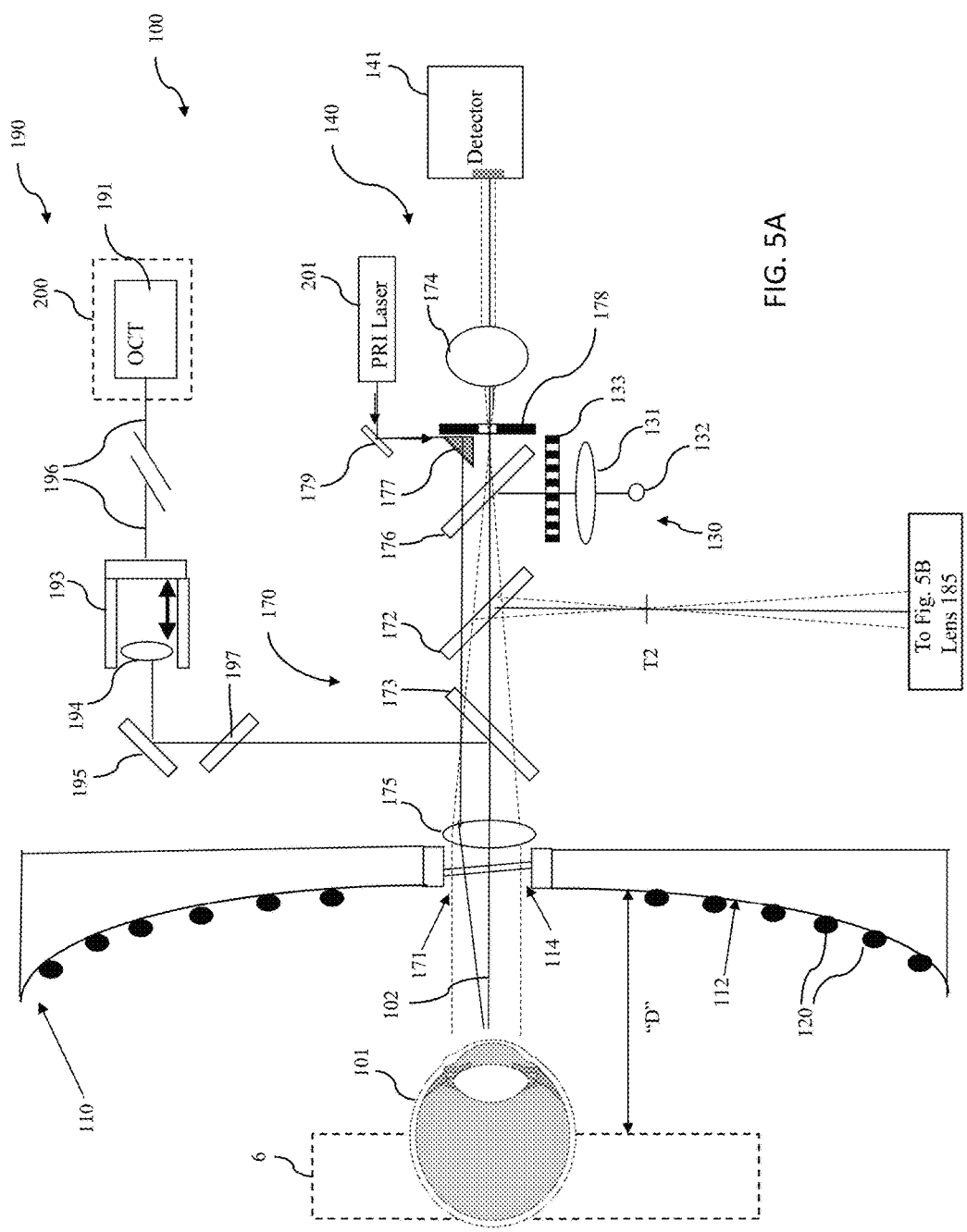
FIGS. 5A and 5B illustrate together an assembly illustrating a suitable configuration and integration of an optical coherence tomographer subsystem, a wavefront aberrometer subsystem a corneal topographer subsystem, an iris imaging subsystem, a fixation target subsystem according to a non-limiting embodiment of the present invention.
Figure 5B:
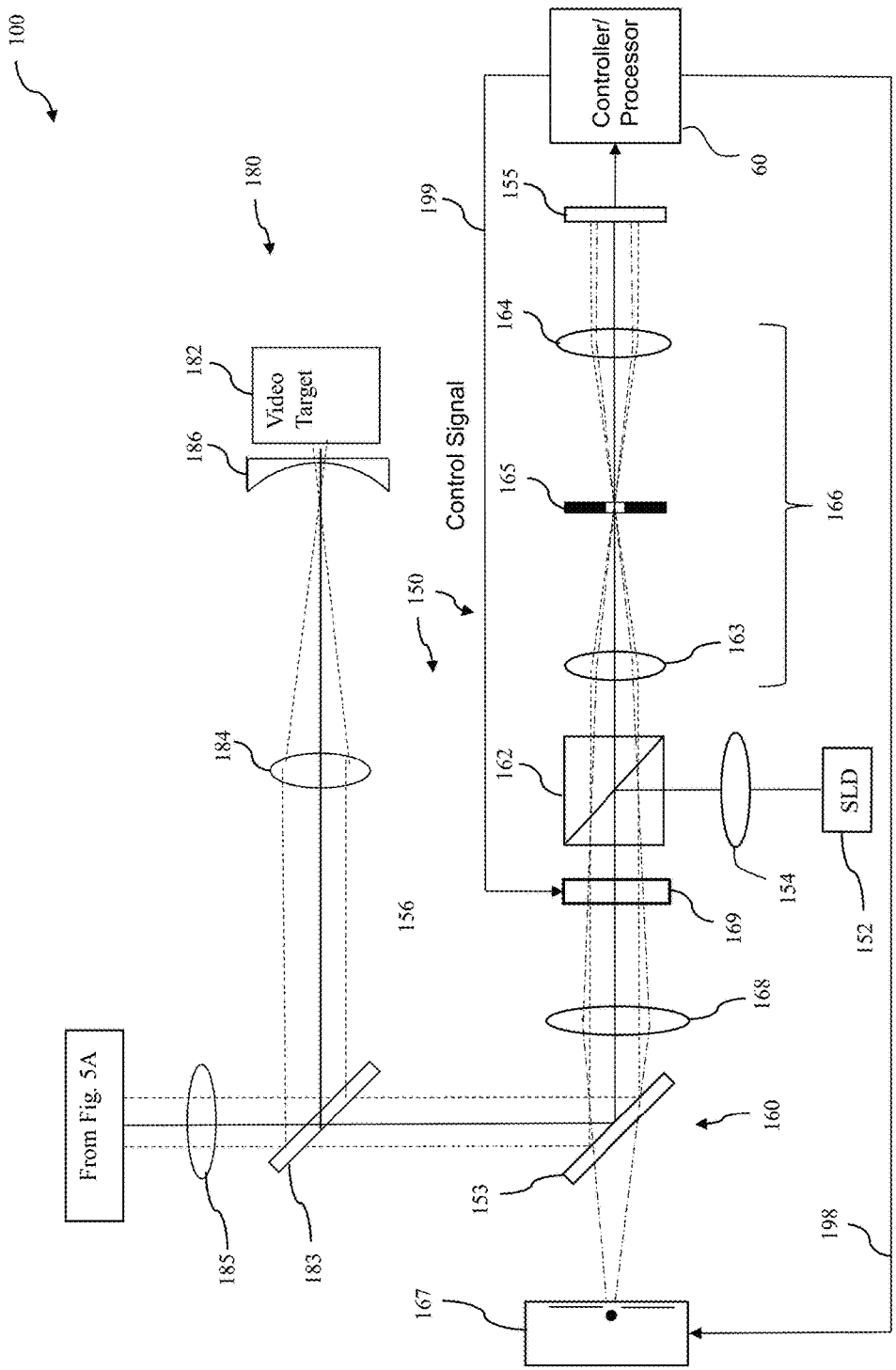

FIGS. 5A and 5B are simplified block diagrams illustrating an assembly 100 according to many embodiments which may be included in system 1. The assembly 100 is a non-limiting example of suitable configurations and integration of the optical coherence tomographer (OCT) subsystem 190, the wavefront aberrometer subsystem 150, the corneal topographer subsystem 140 for measuring one or more characteristics of a subject's eye, a camera 40, the fixation target subsystem 180 and the shared optics.

The shared optics generally comprise one or more components of a first optical system 170 disposed along a central axis 102 passing through the opening or aperture 114 of the structure 110. A first optical system 170 directs light from the various light sources along the central axis 102 towards the eye and establishes a shared or common optical path along which the light from the various light sources travel to the eye 101. In one embodiment, optical system 170 comprises a quarter wave plate 171, a first beamsplitter 172, a second beamsplitter 173, an optical element (e.g., a lens) 174, a second lens 175, a third beamsplitter 176, and a structure including an aperture 178. Additional optical systems may be used in assembly 100 to direct light beams from one or more light sources to the first optical system 170. For example, a second optical system 160 directs light to the first optical system 170 from the wavefront aberrometer subsystem 150 and comprises mirror 153, beam splitter 183 and lens 185.

Other configurations of the assembly 100 may be possible and may be apparent to a person of skill in the art.

The corneal topographer subsystem 140 comprises a structure 110 having a principal surface 112 with an opening or aperture 114 therein; a plurality of first (or peripheral) light sources 120 provided on the principal surface 112 of the structure 110; a Helmholz light source 130; and a detector, photodetector, or detector array 141.

In one embodiment, structure 110 has the shape of an elongated oval or "zeppelin" with openings or apertures at either end thereof. An example of such a structure is disclosed in Yobani Meya-Barbosa et al., "Object surface for applying a modified Hartmann test to measure corneal topography," APPLIED OPTICS, Vol. 40, No. 31 (Nov. 1, 2001) ("Meji'a-Barbosa"). In some embodiments, principal surface 112 of structure 110 is concave when viewed from the cornea of eye 100, as illustrated in FIG. 5A.

In one embodiment where principal surface 112 is concave, principal surface 112 has the shape of a conical frustum. Alternatively, principal surface 112 may have a shape of hemisphere or some other portion of a sphere, with an opening or aperture therein. Also alternatively, principal surface 112 may have the shape of a modified sphere or conical frustum, with a side portion removed. Beneficially, such an arrangement may improve the ergonomics of assembly 100 by more easily allowing structure 110 to be more closely located to a subject's eye 100 without being obstructed by the subject's nose. Of course, a variety of other configurations and shapes for principal surface 112 are possible.

In the embodiment of FIG. 5A, the plurality of first light sources 120 are provided on the principal surface 112 of structure 110 so as to illuminate the cornea of eye 101. In one embodiment, light sources 122 may comprise individual light generating elements or lamps, such as light emitting diodes (LEDs) and/or the tips of the individual optical fibers of a fiber bundle. Alternatively, principal surface 112 of structure 110 may have a plurality of holes or apertures therein, and one or more backlight lamps, which may include reflectors and/or diffusers, may be provided for passing lighting through the holes to form the plurality of first light sources 120 which project light onto the cornea of eye 100. Other arrangements are possible.

In another embodiment, structure 110 is omitted from assembly 100, and the first light sources 120 may be independently suspended (e.g., as separate optical fibers) to form a group of first light sources 120 arranged around a central axis, the group being separated from the axis by a radial distance defining an aperture in the group (corresponding generally to the aperture 114 in the structure 110 illustrated in FIG. 5A).

In operation, a ray (solid line) from one of the first light sources 120 is reflected by the cornea and passes through optical system 170 (including aperture 178) to appear as a light spot on detector array 141. It will be appreciated that this ray is representative of a small bundle of rays that make it through optical system 170 and onto detector array 141, all of which will focus to substantially the same location on detector array 141. Other rays from that first light source 120 are either blocked by the aperture 178 or are otherwise scattered so as to not pass through the optical system 170. In similar fashion, light from the other first light sources 120 are imaged onto detector array 141 such that each one of first light sources 120 is imaged or mapped to a location on detector array 141 that may be correlated to a particular reflection location on the cornea of eye 100 and/or the shape of the cornea. Thus, detector array 141 detects the light spots projected thereon and provides corresponding output signals to a processor of controller 60 (FIG. 2). The processor determines the locations and/or shape of the light spots on detector array 141, and compares these locations and/or shapes to those expected for a standard or model cornea, thereby allowing the processor of controller 60 to determine the corneal topography. Alternatively, other ways of processing the spot images on detector array 141 may be used to determine the corneal topography of eye 101, or other information related to the characterization of eye 101.

Detector array 141 comprises a plurality of light detecting elements arranged in a two dimensional array. In one embodiment, detector array 141 comprises such a charge-coupled device (CCD), such as may be found in a video camera. However, other arrangements such as a CMOS array, or another electronic photosensitive device, may be employed instead. Beneficially, the video output signal(s) of detector array 141 are provided to processor 61 which processes these output signals as described in greater detail below.

Assembly 100 also comprises a Helmholtz light source 130 configured according to the Helmholtz principle. As used herein, the term "Helmholtz source" or "Helmholtz light source" means one or a plurality of individual light sources disposed such that light from each of the individual light sources passes through an optical element having optical power, reflects off of a reference or test object, passes through the optical element, and is received by a detector, wherein light from the Helmholtz source is used to determine geometric and/or optical information of at least a portion of a surface of the reference or test object. In general, it is a characteristic of Helmholtz sources that the signal at the detector is independent of the relative position of the test or reference object relative to the Helmholtz source. As used herein, the term "optical element" means an element that refracts, reflects, and/or diffracts light and has either positive or negative optical power.

In such embodiments, the Helmholtz light source 130 is located at optical infinity with respect to eye 100. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has the Helmholtz light source at optical infinity and the telecentric observing system so that detector array 141 is also optically at an infinite distance from the images of the sources formed by the cornea. Such a measurement system is insensitive to axial misalignment of the corneal surface with respect to the instrument.

In one embodiment, the Helmholtz light source 130 comprises a second light source 132 which may comprise a plurality of lamps, such as LEDs or optical fiber tips. In one embodiment, second light source 132 comprises an LED and a plate 133 with plurality of holes or apertures in a surface that are illuminated by one or more backlight lamps with an optical element 131, which may comprise diffusers.

In one embodiment, second light sources 132 are located off the central optical axis 102 of assembly 100, and light from second light sources 132 is directed toward optical element 171 by third beamsplitter 176.

The operation of the topographer portion of system 100 may be conducted with the combined use of first light source 120 and the Helmholz light source 130. In operation, detector array 141 detects the light spots projected thereon from both Helmholz light source 130 (detected at a central portion of detector array 141) and first light sources 120 (detected at a peripheral portion of detector array 141) and provides corresponding output signals to processor. In general, the images of first light sources 120 that appear on detector array 140 emanate from an outer region of the surface of the cornea, and the images of Helmholz light source 130 that appear on detector array 141 emanate from a central or paraxial region of the surface of the cornea. Accordingly, even though information about the central region of the corneal surface (e.g., surface curvature) cannot be determined from the images of first light sources 120 on detector array 141, such information can be determined from the images of Helmholz light source 130 on detector array 141. A processor of controller 60 determines the locations and/or shapes of the light spots on detector array 141, and compares these locations and/or shapes to those expected based for a standard or model cornea, thereby allowing the processor to determine the corneal topography of eye 101. Accordingly, the topography of the entire corneal surface can be characterized by system 100 without a "hole" or missing data from the central corneal region.

A fourth light source 201 off the central axis 102 may be directed along optical axis 102 by mirrors 177, 179 disposed on or near the aperture 178, perpendicular to the optical axis 102 are configured as a pupil retroreflection illuminator. The pupil retroreflecton illuminator is configured to direct a disc of light toward a patient's eye, whereby the disc of light may be reflected from reflective surfaces within the eye, and the reflected light is transmitted by optical path 170 to detector 141. The pupil retroreflection illuminators may optionally be configured such that, when a patient's pupil is dilated, the disc of light from light source 201 is reflected from an implanted IOL to image the IOL, including any fiducial marks; if IOL is imperfectly placed, detector 141 may be used to determine IOL edges are decentered. Also, images from detector 141 using the pupil retroreflection illuminator may see folds, for instance, unfolded edge if the IOL did not unfold properly.

The wavefront aberrometer subsystem 150 of the assembly 100 comprises a third (probe light beam) light source 152 providing a probe light beam and a wavefront sensor 155. Wavefront aberrometer subsystem 150 may further comprise: a collimating lens 154; a polarizing beamsplitter 163; and an imaging system 166 comprising a first optical element, lens 163 and a second optical element, lens 164, and a dynamic-range limiting aperture 165 for limiting a dynamic range of light provided to wavefront sensor 155 so as to preclude data ambiguity. Light from the wavefront aberrometer subsystem is directed to one of the constituent optical elements of the optical system 170 disposed along a central axis 102 passing through the opening or aperture 114 of the structure 110. It will be appreciated by those of skill in the art that the lenses 163, 164, or any of the other lenses discussed herein, may be replaced or supplemented by another type of converging or diverging optical element, such as a diffractive optical element.

Light source 152 may be an 840 nm SLD (super luminescent laser diode). An SLD is similar to a laser in that the light originates from a very small emitter area. However, unlike a laser, the spectral width of the SLD is very broad, about 40 nm. This tends to reduce speckle effects and improve the images that are used for wavefront measurements.

Wavefront sensor 155 may be a Shack-Hartmann wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

The aperture or opening in the middle of the group of first light sources 120 (e.g., aperture 114 in principal surface 112 of structure 110) allows system 100 to provide a probe light beam into eye 101 to characterize its total ocular aberrations. Accordingly, third light source 152 supplies a probe light beam through a light source polarizing beam splitter 156 and polarizing beam splitter 162 to first beamsplitter 172 of optical system 170. First beamsplitter 172 directs the probe light beam through aperture 114 to eye 101. Beneficially, light from the probe light beam is scattered from the retina of eye 100, and at least a portion of the scattered light passes back through aperture 114 to first beamsplitter 172. First beamsplitter 172 directs the back scattered light back through beam splitter 172 to polarizing beamsplitter 183, mirror 153, adjustable focal length lens 179, and ultimately to wavefront sensor 155.

Wavefront sensor 155 outputs signals to a processor of controller/processor 60 which uses the signals to determine ocular aberrations of eye 101. Beneficially, controller/processor 60 may be able to better characterize eye 101 by considering the corneal topography of eye 101 measured by the corneal topography subsystem, which may also be determined by controller/processor 60 based on outputs of detector array 141, as explained above.

In operation of the wavefront aberrometer subsystem 150, light from light source 152 is collimated by lens 154. The light passes through light source polarizing beam splitter 162. The light entering light source polarizing beam splitter 162 is partially polarized. Polarizing beam splitter 162 reflects light having a first, S, polarization, and transmits light having a second, P, polarization so the exiting light is 100% linearly polarized. In this case, S and P refer to polarization directions relative to the hypotenuse in light source polarizing beam splitter 162.

The light from polarizing beamsplitter 162 travels through adjustable focal length lens 179 and passes through toward beam splitter 153, retaining its S polarization, and then travels through beamsplitter 183, optical element (e.g., lens) 185, beamsplitter 172 and 173, and quarter wave plate 171. Quarter wave plate 171 converts the light to circular polarization. The light then travels through aperture 114 in principal surface 112 of structure 110 to eye 101. Beneficially, the beam diameter on the cornea may be between 1 and 2 mm Then the light travels through the cornea and focuses onto the retina of eye 101.

The focused spot of light becomes a light source that is used to characterize eye 101 with wavefront sensor 155. Light from the probe light beam that impinges on the retina of eye 101 scatters in various directions. Some of the light reflects back as a semi-collimated beam back towards assembly 100. Upon scattering, about 90% of the light retains its polarization. So the light traveling back towards assembly is substantially still circularly polarized. The light then travels through aperture 114 in principal surface 112 of structure 110, through quarterwave plate 171, and is converted back to linear polarization. Quarterwave plate 171 converts the polarization of the light from the eye's retina so that it is P polarized, in contrast to probe light beam having the S polarization. This P polarized light then reflects off of first beamsplitter 172, and passes through optical element (e.g., lens) 185, beamsplitters 183 and 153, optical element (e.g., lens) 168, variable focal length lens 169, and reaches polarizing beamsplitter 162. Since the light is now P polarized relative the hypotenuse of polarizing beamsplitter 162, the beam is transmitted and then continues to imaging system 166 comprising first optical element 164 and second optical element (e.g., lens) 163. The beam is also directed through a dynamic-range limiting aperture 165 for limiting a dynamic range of light provided to wavefront sensor 155 so as to preclude data ambiguity.

When wavefront sensor 155 is a Shack-Hartmann sensor, the light is collected by the lenslet array in wavefront sensor 155 and an image of spots appears on the detector array (e.g., CCD) in wavefront sensor 155. This image is then provided to be processed by controller/processor 60 and analyzed to compute the refraction and aberrations of eye 101.

Similar to what was explained above with respect to wavefront aberrometer 1000, variable focal length lens 169 comprises a pre-correction system which compensates the probe light beam 153 to be injected into eye 101 for aberrations in eye 101 by adding a desired pre-correction for the injected probe light beam 153 by adding defocus that just compensates for the spherical equivalent defocus of eye 101 which is being measured. Variable focal length lens 169 may be a liquid filled lens whose focal length or magnification may be adjusted in response to a focal length control signal (e.g., an electrical signal) 199 which may be provided from controller/processor 60.

The same adjusted focal length for adjustable focal length lens 169 which corrects for the defocus aberrations of eye 101, also ensures that the returned light arrives at a wavefront sensor 155 collimated to within the dynamic range of wavefront sensor 155. Dynamic range limiting aperture 165 blocks any rays outside the angular dynamic range of the wavefront sensor 155 so that no mixing or measurement confusion occurs. When the wavefront sensor 155 is a Shack-Hartmann sensor, the focal spots cannot collide, interfere or cause confusion with adjacent focal spots.

Beneficially, controller/processor 60 controls or adjusts the focal length or magnification of adjustable focal length lens 169 to have an adjusted focal length to provide a desired characteristic to at least one of: probe light beam 153 injected into eye 101, or the light received by wavefront sensor 155 from the retina of eye 101.

The proper or desired adjusted focal length for adjustable focal length lens 169 may be determined in a number of ways. In some embodiments, an additional beam splitter may be provided in an optical path between imaging system 166 and wavefront sensor, and a focusing lens and a detector may be used to create an image of the light incident upon the retina. In that case, the proper or desired adjusted focal length may determined by minimizing the spot size on the back of the retina, performed by comparing the spot sizes from different focal length values for adjustable focal length lens 169. Beneficially eye 101 is arranged to be one focal length of objective lens 168, and wavefront sensor 155 is arranged to be at the conjugate image plane to eye 101.

Meanwhile, controller/processor 60 receives image data ("first image data") from wavefront sensor 155 produced in response to the light returned from the retina of eye 101, and processes the first image data to determine the refraction of eye 101.

However, to correctly determine the refraction of eye 101 from the image data produced by wavefront sensor 155, controller/processor 60 needs to know the adjusted focal length to which adjustable focal length lens 169 was set when the image data was captured.

To address this need, wavefront aberrometer 150 also includes a switchable calibration light source 167 which is configured, when turned on, to provide a calibration light to wavefront sensor 155 via adjustable focal length lens 169. In some embodiments, switchable calibration light source 167 may comprise a switchable LED which passes the calibration light through a pinhole. In some embodiments, switchable calibration light source 167 may be switched ON and OFF in response to a calibration light source control signal 198 (e.g., an electrical signal) from controller/processor 60. In some embodiments, the wavelength of switchable calibration light source 167 may be different than the wavelength of the probe light beam used for the wavefront measurements of eye 101, so long as the focal length or magnification of variable focal length lens 169 is the same at both wavelengths, or at a minimum has a known relationship between the two wavelengths which relationship may be provided to controller/processor 60 (e.g., an offset value stored in memory).

By processing the image data ("second image data") produced by wavefront sensor 155 from the locations of the spots produced on the detector of wavefront sensor 155 in response to the calibration light from calibration light source 167, using standard signal processing techniques, controller/processor 60 may determine the adjusted focal length of adjustable focal length lens 169.

Accordingly, controller/processor 60 may adjust variable focal length lens 169 to a desired or proper adjusted focal length while probe light beam 153 is turned on, as explained above, and while switchable calibration light source 167 may be turned OFF. Then, either before or after (or both, for redundancy) wavefront sensor 155 produces the first image data in response to the light returned from the retina, and while variable focal length lens 169 is still set at the desired or proper adjusted focal length, switchable calibration light source is turned ON and wavefront sensor outputs the second image data produced by wavefront sensor 155 from the locations of the spots produced on the detector of wavefront sensor 155 in response to the calibration light, which may be processed by controller/processor 60 using standard signal processing techniques to determine the adjusted focal length of adjustable focal length lens 169.

Controller/processor 60 may then measure a parameter (e.g., determine a refraction of an aberration) of eye 101 from the first image data produced while variable focal length lens 169 has the adjusted focal length, and from the value of the adjusted focal length itself ascertained from the second image data.

An OCT subsystem 190 of assembly 100 may comprise an OCT assembly 191, and a third optical path 192 which directs the OCT beam of the OCT light source to the first optical path 170. The third optical path 192 may comprise a fiber optic line 196, for conducting the OCT beam from the OCT light source, a z-scan device 193 operable to alter the focus of the beam in the z-direction (i.e., along the direction of propagation of the OCT beam) under control of the controller, and x-scan device 195, and a y-scan device 197 operable to translate the OCT beam in the x and y directions (i.e., perpendicular to the direction of propagation of the of the OCT beam), respectively, under control of the controller. The OCT light source and reference arm may be incorporated into the main unit 4 of the optical measurement instrument 1 shown in FIG. 3A. Alternatively, the OCT assembly 191 may be housed in a second unit 200 and the OCT beam from the OCT source may be directed from the second housing 200 to the main unit by optical pathway 192.

The OCT systems and methods of the optical measurement instruments and methods described herein may be FD-OCT (Fourier domain optical coherence tomography) systems, including either an SD-OCT (spectral domain optical coherence tomography) system or an SS-OCT (swept source optical coherence tomography) system. In conventional FD-OCT systems, the interference signal is distributed and integrated over numerous spectral wavelength intervals, and is inverse Fourier transformed to obtain the depth-dependent reflectivity profile of the sample. The profile of scattering as a function of depth is referred to as an A-scan (Axial-scan). The beam can be scanned laterally to produce a set of A-scans that can be combined together to form a tomogram of the sample (a B-scan).

In an SD-OCT system, various spectral wavelength intervals of the combined returned light from the reference and sample arms are spatially encoded using, for instance, a collimator, diffraction grating, and a linear detector array. Resampling of the data obtained from the linear detector array is performed in order to correct for the nonlinear spatial mapping of wavenumbers. After resampling and subtraction of the dc background, the depth profile structural information is obtained by performing the inverse Fourier transform operation. In swept-source OCT, the broad bandwidth optical source is replaced by a rapid-scanning laser source. By rapidly sweeping the source wavelength over a broad wavelength range, and collecting all the scattering information at each wavelength and at each position, the composition of the collected signal is equivalent to the spectral-domain OCT technique. The collected spectral data is then inverse Fourier transformed to recover the spatial depth-dependent information.

Figure 6:
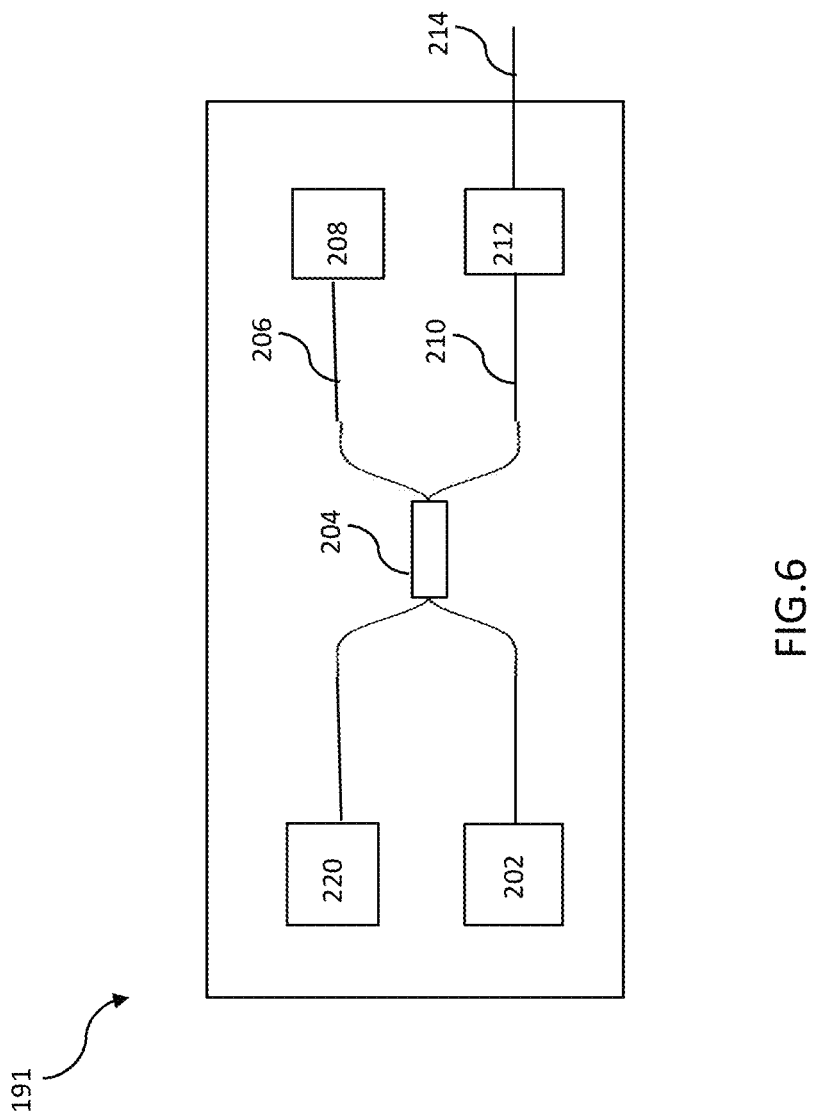
FIG. 6 is a block diagram of an OCT assembly according to many embodiments of the present invention.

FD-OCT suffers from an inherent sample-independent limited depth range, typically between 1 and 5 mm One limitation flows from the fact that FD-OCT extracts depth information from the inverse Fourier transform of a spectral interferogram. Since the spectral interferogram can only be recorded as a real signal, its Fourier transform is necessarily Hermitian symmetric about the zero path length difference (ZPD) position. As a result, the positive and negative displacements about the ZPD cannot be unambiguously resolved, which gives rise to mirror image artifacts and generally halves the useable range. This is referred to as the complex conjugate ambiguity. Another limitation is a sensitivity fall-off which results in reduced sensitivity with increasing depth. Moreover, since the signal in OCT is derived only from backscattered photons, optical attenuation from absorption and scattering generally result in a useable imaging depth of about 1-4 mm Several "full range" OCT techniques have been developed that eliminate the complex conjugate artifacts to effectively double the measurement range around the ZPD position. These full range OCT techniques result in useable imaging depths of up to about 5 mm up to about 8 mm Suitable full range techniques are methods utilizing a dithering reference lag to break the phase ambiguity, methods that use phase distortion, and other suitable methods As shown in FIG. 6, the OCT assembly 191 of OCT subsystem 190 includes a broadband or a swept light source 202 that is split by a coupler 204 into a reference arm 206 and a sample arm 210. The reference arm 106 includes a module 108 containing a reference reflection along with suitable dispersion and path length compensation. The sample arm 110 of the OCT assembly 191 has an output connector 212 that serves as an interface to the rest of the optical measurement instrument. The return signals from both the reference and sample arms 206, 210 are then directed by coupler 204 to a detection device 220, which employs either time-domain, frequency, or single point detection techniques. In FIG. 6, a swept source technique is used with a laser wavelength of 1060 nm swept over a range of 8-50 mm depth.

Figure 7:
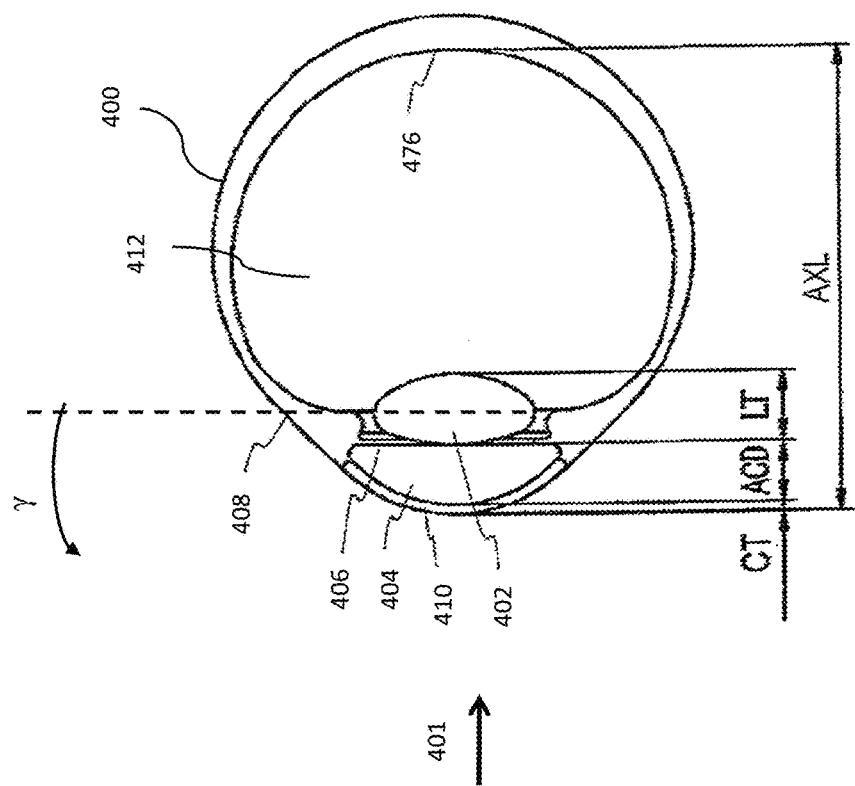
FIG. 7 is a schematic drawing of a human eye.

FIG. 7 is a schematic drawing of a human eye 400. In many embodiments, a light beam 401 from a light source enters the eye from the left of FIG. 7, refracts into the cornea 410, passes through the anterior chamber 404, the iris 406 through the pupil, and reaches lens 402. After refracting into the lens, light passes through the vitreous chamber 412, and strikes the retina 476, which detects the light and converts it to an electric signal transmitted through the optic nerve to the brain (not shown). The vitreous chamber 412 contains the vitreous humor, a clear liquid disposed between the lens 402 and retina 476. As indicated in FIG. 7, cornea 410 has corneal thickness (CT), here considered as the distance between the anterior and posterior surfaces of the cornea. Anterior chamber 404 has anterior chamber depth (ACD), which is the distance between the anterior surface of the cornea and the anterior surface of the lens. Lens 402 has lens thickness (LT) which is the distance between the anterior and posterior surfaces of the lens. The eye has an axial length (AXL) which is the distance between the anterior surface of the cornea and the retina 476. FIG. 7 also illustrates that, in many subjects the lens, including the lens capsule, may be tilted at one or more angles relative to the optical axis, including an angle y relative to the optical axis of the eye.

The optical system may also be arranged so that the movement pattern of the scan mirrors provides a lateral motion across the retina so that the shape of the retina may be determined. It is of particular interested to measure the shape and location of the depressed region of the retina named the foveal pit. When the patient is looking directly into the instrument, with their line of sight aligned to the fixation target, the foveal pit will be in center of the OCT lateral scan. This information is beneficial in that it informs the instrument operator if the patient was looking directly at the target when the measurement was made. Retinal scans are also useful in detecting disease conditions. In some cases there may be an absence of a foveal pit that also is considered an indication of a corneal abnormality.

The average axial length of the adult human eye is about 24 mm Since the full range imaging depth of the OCT measurements are only about 5 mm to 8 mm, then OCT scanning may provide for OCT scans at different depths of the eye that can be combined together to form a combined OCT image of the eye. The OCT measurements may include OCT imaging at various depths of the patient's eye for imaging: (1) at least a portion of the retina, (2) at least a portion of the anterior portion of the eye, including at least a portion of the cornea (anterior and posterior), iris, and lens (anterior and posterior), and (3) performing axial eye length measurements.

FIGS. 7A-7C illustrate various aspects of the OCT subsystem 190 according to various aspects of the present invention. FIG. 8A illustrates a preferred scanning region for the OCT subsystem according to many embodiments of the present invention. The scanning region may be defined from starting point 301 to ending point 302 at the anterior portion of the eye extending in a direction transverse the direction of propagation of the OCT beam and also extending in a direction parallel to an axis defining the axial length of the eye to the posterior portion 304 of the eye. The lateral scanning region should generally be sufficiently large in the lateral direction to permit imaging of the central portion of the cornea, at least a portion of the iris, at least a portion of the lens and at least of the retina. It should be noted that a region 303 between the posterior portion of the lens and the surface of the retina may optionally not be scanned by OCT subsystem 190 because the portion 330 does not contain anatomical structure for 3D analysis.

FIG. 6B shows a representative graph of an intensity of an OCT signal of an OCT subsystem 190 according to many embodiments as a function of depth along the axis defining the axial length of the eye. The graph generally exhibits approximately four peaks having a complex structure: (1) a peak 310 having a doublet-like structure and generally corresponding to a location of the cornea; (2) a peak 320 having a doublet-like structure and generally corresponding to a location of an anterior surface of the lens; (3) a peak 330 having a complex structure generally corresponding to a location of a posterior surface of the lens; and (4) a peak 340 generally corresponding to a location of a retina. A distance between peak 310 and peak 340 can be used to calculate the axial length (AL) of the eye. An OCT scan by OCT subsystem 190, including both an A-scan and B-scan, may be conducted for at least one location in the anterior portion of the eye (e.g., a location of a cornea, a location of an anterior surface of a lens and/or a location of a posterior surface of the lens) and at least one location in the posterior portion of the eye (e.g., at a location of a retina). In some embodiments, an OCT scan by the OCT subsystem 190, including both an A-Scan and a B-scan is performed at a location corresponding to each of a location of the cornea, a location of an anterior surface of the lens, a location of a posterior surface of the lens, and a location corresponding to a retina.

It should be noted that because the OCT subsystem 190 provides for the detection of various structures of the eye, including a location of the cornea, the OCT subsystem 190 may be used as a ranging system to precisely align the patient in relation to the optical measurement system 1 of the present invention. The use of the OCT as a ranging system can significantly improve accuracy of corneal topography measurements, including keratometry measurements, which are sensitive to misalignment of the corneal structures.

FIG. 6C shows a cross-section of an eye obtained by an optical measurement system of the present invention using an OCT subsystem according to the present invention.

Figure 9:
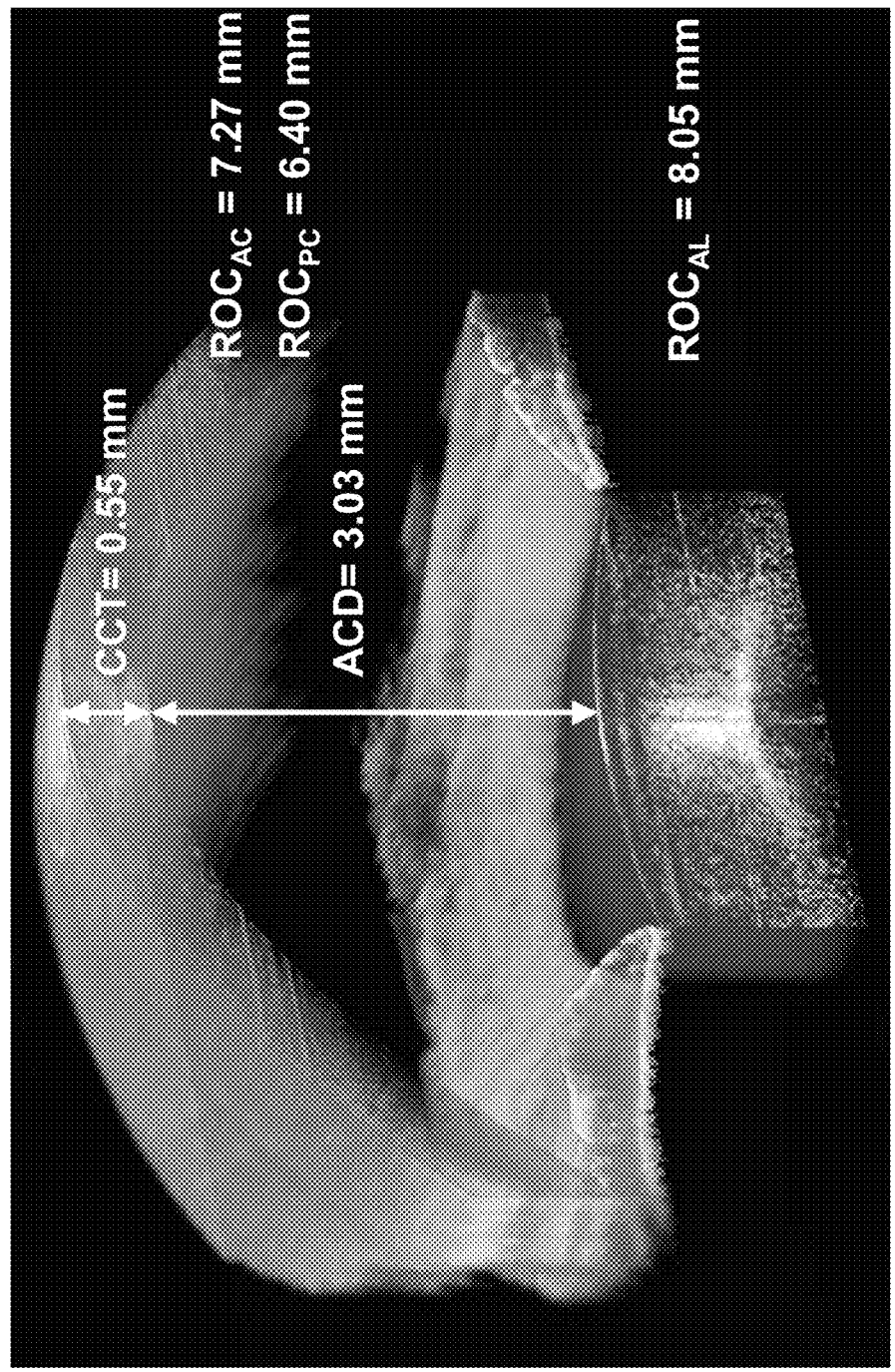
FIG. 9 is a 3-dimensional representation of an anterior portion of an eye obtained using the optical measurement system according to many embodiments.

FIG. 7 shows a 3 dimensional view of an eye obtained by an optical measurement system of the present invention using an OCT subsystem according to the present invention. FIG. 9 evidences that the OCT subsystem of the present invention is operable to obtain biometry measurements according to the present invention, including the central corneal thickness (CCT), the anterior chamber depth (ACD), the radius of curvature of the anterior cornea ($ROC_{AC}$), the radius of curvature of the Posterior cornea ($ROC_{pc}$) and the Radius of curvature of the axial length ($ROC_{AL}$).

OCT subsystem 190 may provide sufficiently resolved structural information to a structural assessment that may provide a user with an indication of suitability of a particular patient for a laser cataract procedure. In one embodiment, an OCT scan performed by the OCT subsystem 190 at or near the retina (i.e., a retina scan) is sufficiently resolved to identify the foveal pit location and depth, wherein a lack of depression indicates an unhealthy retina.

In another embodiment, the optical measurement instrument 1 of the present invention provides one or more measurements sufficient to provide an assessment of the tear film of a patient. In one embodiment, the tear film assessment comprises a comparison of a wavefront aberrometry map and a corneal topography map or OCT map of the patient's eye, by, for instance, subtracting the corneal topography map from the wavefront aberrometry map, to obtain a difference map. A determination of whether the tear film is broken (if not smooth); an assessment of the tear film, including tear film breakup, can be obtained by reviewing the shape of spots on the topographer. For instance, a finding or indication that the tear film is disrupted, or broken, may be based upon the shape of a spot in that, if the spots are not round, and have, for instance, an oblong or broken up shape, it indicates that tear film is disrupted. The existence of such a disrupted tear film may indicate that K value, and other ocular measurements may not be reliable In operation, as shown in FIG. 5A, after exiting connector 212, the OCT beam 214 may be collimated, for example using a collimating optical fiber 196. Following collimating fiber 196 the OCT beam 214 is directed to an z-scan device 193 operable to change the focal point of the OCT beam in a z-direction, and x- and y-scan devices 195 and 197, which are operable to scan the OCT beam in x and y-directions perpendicular to the z-direction.

Following the collimating optical fiber 196, the OCT beam 214 continues through a z-scan device 193, 194. The z-scan device may be a Z telescope 193, which is operable to scan focus position of the laser pulse beam 66 in the patient's eye 101 along the Z axis. For example, the Z-telescope may include a Galilean telescope with two lens groups (each lens group includes one or more lenses). One of the lens groups moves along the Z axis about the collimation position of the Z-telescope 193. In this way, the focus position in the patient's eye 101 moves along the Z axis. In general, there is a relationship between the motion of lens group and the motion of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as a z-scan device for changing the focus point of the OCT beam 214 in the patient's eye 101. The Z-scan device can be controlled automatically and dynamically by the controller 60 and selected to be independent or to interplay with the X and Y scan devices described next.

After passing through the z-scan device, the OCT beam 214 is incident upon an X-scan device 195, which is operable to scan the OCT beam 214 in the X direction, which is dominantly transverse to the Z axis and transverse to the direction of propagation of the OCT beam 214. The X-scan device 195 is controlled by the controller 60, and can include suitable components, such as a lens coupled to a MEMS device, a motor, galvanometer, or any other well-known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 196, the OCT beam 214 is incident upon a Y scan device 197, which is operable to scan the OCT beam 214 in the Y direction, which is dominantly transverse to the X and Z axes. The Y-scan device 197 is controlled by the controller 60, and can include suitable components, such as a lens coupled to a MEMS device, motor, galvanometer, or any other well-known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 195 and the Y-Scan device 197 can be provided by an XY-scan device configured to scan the laser pulse beam 66 in two dimensions transverse to the Z axis and the propagation direction of the laser pulse beam 66. The X-scan and Y scan devices 195, 197 change the resulting direction of the OCT beam 214, causing lateral displacements of OCT beam 214 located in the patient's eye 101.

The OCT sample beam 214 is then directed to beam splitter 173 through lens 175 through quarter wave plate 171 and aperture 114 and to the patient eye 101. Reflections and scatter off of structures within the eye provide return beams that retrace back through the patient interface quarter wave plate 171, lens 175, beam splitter 173, y-scan device 197, x-scan device 195, z-scan device 193, optical fiber 196 and beam combiner 204 (FIG. 3), and back into the OCT detection device 220. The returning back reflections of the sample arm 201 are combined with the returning reference portion 206 and directed into the detector portion of the OCT detection device 220, which generates OCT signals in response to the combined returning beams. The generated OCT signals that are in turn interpreted by the controller 60 to determine the spatial disposition of the structures of interest in the patient's eye 101. The generated OCT signals can also be interpreted by the controller to determine the spatial disposition of the structures of interest in the patient's eye 101. The generated OCT signals can also be interpreted by the control electronics to align the position and orientation of the patient eye within the patient interface.

Optical measurement systems disclosed herein may comprise an iris imaging subsystem 40. The imaging subsystem 40 generally may comprise an infrared light source, for example an infrared light source 152, and detector 141. In operation light from the light source 152 is directed along second optical path 160 to first optical path 170 and is subsequently directed to eye 101 as described above. Light reflected from the iris of eye 101 is reflected back along first optical path 170 to detector 141. In normal use, an operator will adjust a position or alignment of system 100 in XY and Z directions to align the patient according to the image detector array 141. In one embodiment of the iris imaging subsystem, eye 101 is illuminated with infrared light from light source 152. In this way, the wavefront obtained by wavefront sensor 155 will be registered to the image from detector array 141.

The image that the operator sees is the iris of eye 100. The cornea generally magnifies and slightly displaces the image from the physical location of the iris. So the alignment that is done is actually to the entrance pupil of the eye. This is generally the desired condition for wavefront sensing and iris registration.

Iris images obtained by the iris imaging subsystem may be used for registering and/or fusing the multiple data sets obtained by the various subsystems of the present invention, by methods described for instance in "Method for registering multiple data sets," U.S. patent application Ser. No. 12/418,841, which is incorporated herein by reference. As set forth in application Ser. No. 12/418,841, wavefront aberrometry may be fused with corneal topography, optical coherence tomography and wavefront, optical coherence tomography and topography, pachymetry and wavefront, etc. For instance, with image recognition techniques it is possible to find the position and extent of various features in an image. Regarding iris registration images, features that are available include the position, size and shape of the pupil, the position, size and shape of the outer iris boundary (OIB), salient iris features (landmarks) and other features as are determined to be needed. Using these techniques, both patient movement between measurements (and/or during a measurement sequence) can be identified, as well as changes in the eye itself (including those induced by the measurement, such as changes in the size of the pupil, changes in pupil location, etc.).

In many embodiments, an optical measurement system according the present includes a target fixation subsystem 50 (FIG. 4), and an assembly 100 shown in FIGS. 5A and 5B includes fixation target subsystem 180 which includes a fixation target 182 for the patient to view. Fixation target subsystem 180 is used to control the patient's accommodation, because it is often desired to measure the refraction and wavefront aberrations when eye 100 is focused at its far point (e.g., because LASIK treatments are primarily based on this). In the target fixation subsystem, a projection of a target, for instance a cross-hair pattern is projected onto the eye of the patient, the cross hair pattern being formed by a backlit LED and a film.

In operation, light originates from the light source 152 or, alternatively, from video target backlight 182 and lens 186. Lens 185 collects the light and forms an aerial image T2. This aerial image is the one that the patient views. The patient focus is maintained on aerial image 182 during measurement so as to maintain the eye in a fixed focal position.

The operating sequence the optical measurement system and methods of the present is not particularly limited. A scan of the patient's eye may comprise one or more of a wavefront aberrometry measurement of a patient's eye utilizing the wavefront aberrometry subsystem, a corneal topography measurement of a patient's eye and an OCT scan of the patient's eye using the OCT subsystem, wherein the OCT scan includes a scan at each or one or more locations within the eye of the patient. These locations of the OCT scan may correspond to the location of the cornea, the location of the anterior portion of the lens, the location of the posterior portion of the lens and the location of the retina. In a preferred embodiment, the operating sequence includes each of a wavefront aberrometry measurement, a corneal topography measurement and an OCT scan, wherein the OCT scan is taken at least at the retina, the cornea and one of anterior portion of the patient's lens. An iris image may be taken simultaneously with or sequentially with an each of measurements taken with wavefront aberrometry subsystem the corneal topography subsystem and the OCT subsystem, including an iris image take simultaneously with or sequentially with the location of each OCT scan. This results in improved accuracy in the 3-dimensional modeling of the patient's eye by permitting the various data sets to be fused and merged into a 3-dimensional model.

FIG. 10 shows one embodiment of an operating sequence and method in which wavefront aberrometry measurements, corneal topography measurements and OCT measurements are all taken. The optical measurement apparatus, including the method of FIG. 10 may be used preoperatively, intraoperatively and/or postoperatively. In the method of FIG. 10, a step 801 comprises aligning the optical measurement system to the eye of the patent. A step 805 comprises activating the Target Fixation subsystem for patient fixation on target. A step 810 comprises activating the wavefront aberrometer subsystem such that the wavefront aberrometer light source 810 is activated and the eye refraction is measured via the wavefront sensor. A step 815 comprises activating the target fixation system to move the target to an optimum position and activate the wavefront aberrometer subsystem such that the wavefront aberrometer light source 152 is activated and the eye refraction is measured via the wavefront sensor 155. A step 820 comprises obtaining an iris image using Iris Imaging Subsystem while infrared light source 152 is operating. A step 825 comprises operating the z-scan device to set OCT scan location at or near cornea, and performing an OCT Scan with the OCT Subsystem. A step 830 comprises operating the z-scan device to set the OCT location at a location at or near the lens anterior and performing an OCT Scan with the OCT Subsystem. A step 835 comprises operating the z-scan device to set the OCT location at a location at or near the lens posterior and performing an OCT Scan with the OCT Subsystem. A step 840 comprises operating the X-scan device and Y-scan device so no light from OCT reaches detector 141. A step 845 comprises obtaining an iris image using the Iris Imaging Subsystem while the infrared light source 152 flashes. A step 850 comprises obtaining an iris image using the Iris Imaging Subsystem while the light sources 120 and Helmholz source flash. A step 855 comprises measuring the corneal topography with the Corneal Topography Subsystem. A step 855 comprises operating the z-scan device to set the OCT location at a location at or near the retina and performing an OCT Scan with the OCT Subsystem. A step 860 comprises operating the X-scan device and Y-scan device so no light from OCT reaches detector 141. An optional step 865 comprises measuring corneal topography with Corneal Topography Subsystem, which may provide for an improved 3D model of the patient eye. An optional step 870 comprises obtaining an iris image using Iris Imaging Subsystem (for 3D model).

The optical measurement instrument 1 and the optical measurements obtained therewith may be used pre-operatively, i.e. before a cataract surgery or other surgical procedure, for, e.g., eye biometry and other measurements, diagnostics and surgical planning Surgical planning may include one or more predictive models. In the one or more predictive models, one or more characteristics of the postoperative condition of the patient's eye or vision is modeled based on one or more selected from the group consisting of pre-operative measurements obtained from the optical measurement instrument 1, a contemplated surgical intervention, and on or more algorithms or models stored in the memory of the optical measurement system 1 and executed by the processor. The contemplated surgical intervention may include the selection of an IOL for placement, the selection of an IOL characteristic, the nature or type of incision to be used during surgery (e.g., relaxation incision), or one or more post-operative vision characteristics requested by the patient.

The optical measurement instrument 1 and the optical measurements obtained therewith may be used intra-operatively, i.e., during a cataract surgery or other surgical procedure, for, e.g., intraoperative eye diagnostics, determining IOL placement and position, surgical planning, and control/or of a laser surgical system. For instance, in the case of laser cataract surgical procedure, any measurement data obtained preoperatively by the optical measurement instrument may be transferred to a memory associated with a cataract laser surgical system for use before, during or after either the placement of a capsulotomy, fragmentation or a patient's lens or IOL placement during the cataract surgery. In some embodiments, measurements using optical measurement instrument 1 may be taken during the surgical procedure to determine whether the IOL is properly placed in the patient's eye. In this regard, conditions measured during the surgical procedure may be compared to a predicted condition of the patient's eye based on pre-operative measurements, and a difference between the predicted condition and the actual measured condition may be used to undertake additional or corrective actions during the cataract surgery or other surgical procedure.

The optical measurement instrument 1 and the optical measurements obtained therewith may be used postoperatively, i.e., after a cataract surgery or other surgical procedure, for, e.g., post-operative measurement, postoperative eye diagnostics, postoperative IOL placement and position determinations, and corrective treatment planning if necessary. The postoperative testing may occur sufficiently after the surgery that the patient's eye has had sufficient time to heal and the patient's vision has achieved a stable, postsurgical state. A postoperative condition may be compared to one or more predicted condition performed pre-operatively, and a difference between the preoperatively predicted condition and the postoperatively measured condition may be used to plan additional or corrective actions during the cataract surgery or other surgical procedure.

The optical measurement instrument 1, including the corneal topography subsystem, the OCT subsystem and the wavefront aberrometry subsystem, utilizing a suitable operating sequence as disclosed herein, is operable to measure one, more than one or all of the following: ocular biometry information, anterior corneal surface information, posterior corneal surface information, anterior lens surface information, posterior lens surface information, lens tilt information and lens position information. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory 62 associated with controller 60. The plurality of characteristics may be measured preoperatively, and where appropriate, intra-operatively, and postoperatively.

In some embodiments, memory 62 associated with controller 60 may store intraocular lens (IOL) model data for a plurality of IOL models, each of the IOL models having associated with it a plurality of predetermined parameters selected from the group consisting of dioptic power, refractive index, asphericity, toricity, haptic angulation and lens filter. The IOL data may be used by one or more processors of optical measurement instrument 1, in conjunction with measurement data of a subject's eye obtained by optical measurement instrument 1, for cataract diagnostics or cataract treatment planning, which may include specifying and/or selecting a particular IOL for a subject's eye. For example, one or more processors of optical measurement instrument 1 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria.

In some embodiments, one or more processors of optical measurement instrument 1 may execute an algorithm comprising: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

In many embodiments, the eye imaging and diagnostic system further comprises a memory operable to store Intraocular Lens ("IOL") Data, the IOL data including a plurality of dioptic power, anterior and posterior radius, IOL thickness, refractive index, asphericity, toricity, echelette features, haptic angulation and lens filter.

In many embodiments, the eye imaging and diagnostic system further comprises a memory operable to store intraocular lens ("IOL") model data for a plurality of IOL models, IOL model having associated with a plurality of predetermined parameters selected from the group consisting of dioptic power, anterior and posterior radius, IOL thickness, refractive index, asphericity, toricity, echelette features, haptic angulation and lens filter.

An improved system for selecting an intraocular lens (IOL) for implantation, comprises: a memory operable to store data acquired from each of the corneal topography subsystem, the wavefront sensor subsystem and the Optical Coherence Tomography subsystem, wherein the stored data includes a plurality of ocular biometry information, anterior corneal surface information, posterior corneal surface information, anterior lens surface information, and posterior lens surface information, lens tilt information and lens position information; the memory further operable to store intraocular lens ("IOL") model data for a plurality of IOL models, IOL model having associated with it a plurality of predetermined parameters selected from the group consisting of dioptic power, anterior and posterior radius, IOL thickness, refractive index, asphericity, toricity, echelette features, haptic angulation and lens filter; and a processor coupled to the memory, the processor deriving the treatment of the eye of the patient applying, for each of the plurality of identified IOL Model, to: (1) predict a position of one of the identified IOL Models when implanted in the subject eye, based on the plurality of characteristics; (2) simulate the subject eye based on the plurality of IOL predetermined parameters and the predicted IOL position; (3) perform one or more of ray tracing and a IOL spherical equivalent (SE) and cylinder (C) power calculation, as well as optionally, to determine the optimum IOL orientation based on said eye model; and (4) propose one IOL power for one or more IOL models from the plurality of IOLs corresponding to the optimized IOL(s) based on predetermined criteria; and (5) show the simulated optical quality and/or visual performance provided by each of the proposed IOL models for distance and/or for any other vergence.

A method of selecting an intraocular lens (IOL) to be implanted in a subject's eye, comprising: measuring a plurality of eye characteristics comprising ocular biometry information, anterior corneal surface information, posterior corneal surface information, anterior lens surface information, and posterior lens surface information, lens tilt information and lens position information; and for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) modeling the subject eye with the intraocular lens; (2) simulating the subject eye based on the plurality of IOL predetermined parameters and the predicted IOL position; (3) performing a ray tracing and a IOL spherical equivalent (SE) and cylinder (C) power calculation, as well as determine the optimum IOL orientation based on said eye model; and (4) proposing one IOL power for one or more IOL models from the plurality of IOLs corresponding to the optimized IOL(s) based on predetermined criteria; and optionally (5) show the simulated optical quality and/or visual performance provided by each of the proposed IOL models for distance and/or for any other vergence.

A tangible computer-readable storage device storing computer instructions which, when read by a computer, cause the computer to perform a method comprising: receiving a plurality of eye characteristics comprising ocular biometry information, anterior corneal surface information, posterior corneal surface information, anterior lens surface information, and posterior lens surface information, lens tilt information and lens position information; for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) simulating a geometry of the subject eye with each of the plurality of intraocular lenses (IOL) implanted, in accordance with the plurality of eye characteristics; (2) performing a ray tracing and a IOL spherical equivalent (SE) and cylinder (C) power calculation, as well as optionally determining the optimum IOL orientation based on said eye model; (3) proposing one IOL power for one or more IOL models from the plurality of IOLs corresponding to the optimized IOL(s) based on predetermined criteria; and optionally (4) showing the simulated optical quality and/or visual performance provided by each of the proposed IOL models for distance and/or for any other vergence.

A method of predicting the intraocular lens position comprising: determining a plurality of eye characteristics before cataract surgery, comprising ocular biometry information, anterior corneal surface information, posterior corneal surface information, anterior lens surface information, and posterior lens surface information, lens tilt information and lens position information; determining a plurality of eye characteristics after cataract surgery, comprising ocular biometry information, anterior corneal surface information, posterior corneal surface information, anterior lens surface information, and posterior lens surface information, lens tilt information and lens position information; calculating or measuring, based on a mathematical relationship, a distance from the apex to a plane of the intraocular lens after an ocular surgical procedure; calculating an optical power of the intraocular lens suitable for providing a predetermined refractive outcome; wherein a mathematical relationship is found between the preoperative and postoperative eye characteristics that accurately predict the measured distance from the apex to the plane where the intraocular lens is.

An improved system for planning a refractive treatment of an eye of a patient, the system comprising: a memory operable to store eye measurement data comprising ocular biometry information, anterior conical surface information, posterior corneal surface information, anterior lens surface information, and posterior lens surface information, lens tilt information and lens position information; a processor coupled to the memory, the processor deriving the treatment of the eye of the patient applying an effective treatment transfer function, wherein the effective treatment transfer function is derived from, for each of a plurality of prior eye treatments, a correlation between a pre-treatment vector characterizing the eye measurement data before treatment, and a post-treatment vector characterizing post-treatment eye measurement data of the associated eye; an output coupled to the processor so as to transmit the treatment to facilitate improving refraction of the eye of the patient. The processor may comprise tangible media embodying machine readable instructions for implementing the derivation of the treatment.

An improved method for planning a refractive treatment of an eye of a patient, the system comprises: measuring a plurality of ocular biometry information, anterior corneal surface information, posterior conical surface information, anterior lens surface information, and posterior lens surface information, lens tilt information and lens position information.

A method of customizing at least one parameter of an intraocular lens, comprising: measuring a plurality of eye characteristics comprising ocular biometry information, anterior conical surface information, posterior conical surface information, anterior lens surface information, and posterior lens surface information, lens tilt information and lens position information; determining a desired postoperative condition of the eye; empirically calculating a postoperative condition of the eye based at least partially on the measured eye characteristics; and predictively estimating, in accordance with an output of said empirically calculating and the eye characteristics, the at least one parameter of the intraocular lens to obtain the desired postoperative condition.

A method of adjusting the refractive power in an eye of a patient who has undergone cataract surgery comprising: measuring a plurality of post-operative eye characteristics in an eye of a patient who has previously undergone cataract surgery, the eye characteristics comprising ocular biometry information, anterior corneal surface information, posterior conical surface information, anterior lens surface information, and posterior lens surface information, lens tilt information and lens position information; identifying a plurality of corrective procedure based at least partially on one of (1) a comparison of at least one measured pre-operative eye characteristic and the corresponding measured post-operative eye characteristic; and (2) a comparison of at least one predicted post-operative eye characteristic and the corresponding measured post-operative eye characteristic; for each of a plurality of corrective procedures: modeling the subject eye with the corrective procedure; modeling the subject eye based on the corrective procedure; performing one of a ray tracing and a power calculation based on said eye model; and selecting a corrective procedure from the plurality of IOL models corresponding to the optimized IOL based on a predetermined criteria.

In some embodiments, the system further comprises a processor configured to execute an algorithm. The algorithm comprises, for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL from the plurality of IOL models corresponding to the optimized IOL based on a predetermined criteria.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

All patents and patent applications cited here are hereby incorporated by reference hereference in their entirety.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A system, comprising:
   a first light source producing a probe light beam to be injected into an eye;
   a pre-correction system which compensates the probe light beam to be injected into the eye for aberrations in the eye, the pre-correction system being positioned in an optical path between the first light source and the eye, the pre-correction system including a variable focal length lens;
   a processor configured to adjust a focal length of the variable focal length lens;
   a switchable calibration light source disposed at a known position with respect to the variable focal length lens and configured to provide a calibration light beam to the variable focal length lens; and
   a wavefront sensor configured to receive light returned from a retina of the eye in response to the probe light beam, and in response thereto to output first image data, and to receive the calibration light from the variable focal length lens when the switchable calibration light source is on, and in response thereto to output second image data,
   wherein the processor is configured to receive the first image data,
   wherein the processor is further configured to adjust the focal length of the variable focal length lens to have an adjusted focal length so as to provide a desired characteristic to at least one of: the probe light beam injected into the eye, and the light received by the wavefront sensor from the retina,
   wherein the processor is further configured to switch on the switchable calibration light source while the variable focal length lens has the adjusted focal length, and to ascertain the adjusted focal length of the variable focal length lens from the second image data output from the wavefront sensor in response to the calibration light received from switchable calibration light source, and
   wherein the processor is further configured to determine an aberration of the eye from the first image data produced while the variable focal length lens has the adjusted focal length, and from the adjusted focal length ascertained from the second image data.

2. The system of claim 1, wherein the wavefront sensor is a Shack-Hartmann wavefront sensor.

3. The system of claim 1, wherein the wavefront sensor is one of a shearing interferometer and a Moiré deflectometer.

4. The system of claim 1, further comprising an imaging system which collects the light returned from the retina of the eye in response to the probe light beam and provides the light to the wavefront sensor, and which collects the calibration light beam when the switchable calibration light source is on and provides the calibration light to the wavefront sensor, wherein the imaging system comprises a telescope having two lens spaced apart from each other.

5. The system of claim 4, comprising a dynamic range limiting aperture disposed in an optical path between the two lenses of the telescope.

6. The system of claim 5, wherein said telescope is arranged so that one lens of the telescope is one focal length away from the eye.

7. The system of claim 1, wherein the variable focal length lens comprises one selected from: a liquid filled lens; an electrostatic membrane lens; and one or more optomechanical elements.

8. The system of claim 1, wherein the pre-correction system corrects for focus errors in the eye.

9. The system of claim 1, wherein the pre-correction system corrects for focus and astigmatism.

10. The system of claim 1, wherein the desired characteristic is a minimized waveform error at the wavefront sensor.

11. The system of claim 1, wherein the processor is further configured to adjust the focal length of the variable focal length lens in response to the first image data, and wherein the desired characteristic is collimation of the light received by the wavefront sensor.

12. The system of claim 1, further comprising at least one of an optical coherence tomographer and a corneal topographer.

13. The system of claim 1, wherein the first light source, pre-correction system, processor, and wavefront sensor comprise a wavefront aberrometer, the system further comprising both an optical coherence tomographer and a corneal topographer, wherein all of the wavefront aberrometer, optical coherence tomographer and corneal topographer share a common lens for receiving light returning from the eye.

14. The system of claim 13, wherein the wavefront aberrometer, optical coherence tomographer and corneal topographer all employ the common lens for directing at least some light to the eye.

15. The system of claim 13, wherein the corneal topographer comprises a plurality of peripheral light sources disposed on a principal surface of a structure having an aperture therein, and wherein the common lens is disposed in an optical path from the eye which passes through the aperture.

16. A method, comprising:
passing a probe light beam to an eye, and returning light from a retina of the eye through a variable focal length lens to a wavefront sensor;
adjusting a focal length of the variable focal length lens to provide a desired characteristic to at least one of: the probe light beam provided to the eye, and the light returned by the retina to the wavefront sensor;
while the variable focal length lens is at the adjusted focal length, passing a calibration light through the variable focal length lens to the wavefront sensor to ascertain at least one parameter of the variable focal length lens, including at least one of: the adjusted focal length, an astigmatism of the variable focal length lens, and a higher order wavefront aberration of the variable focal length lens; and
making a wavefront measurement of the eye from the light returned from the retina of the eye through the variable focal length lens to the wavefront sensor while the variable focal length lens has the adjusted focal length, and from the at least one parameter of the variable focal length lens ascertained from the calibration light received by the wavefront sensor.

17. The method of claim 16, comprising passing the calibration light through the variable focal length lens to the wavefront sensor to ascertain the at least one parameter of the variable focal length lens after returning the light from the retina of the eye through the variable focal length lens to the wavefront sensor.

18. The method of claim 17, wherein the calibration light is provided by a switchable calibration light source, the method further comprising:
switching off the calibration light source while returning the light from the retina of the eye through the variable focal length lens to a wavefront sensor; and
subsequently switching on the calibration light source after returning the light from the retina of the eye through the variable focal length lens to the wavefront sensor to ascertain the at least one parameter of the variable focal length lens.

19. The method of claim 16, comprising passing the calibration light through the variable focal length lens to the wavefront sensor to ascertain the at least one parameter of the variable focal length lens prior to returning the light from the retina of the eye through the variable focal length lens to the wavefront sensor.

20. The method of claim 19, wherein the calibration light is provided by a switchable calibration light source, the method further comprising:
switching on the calibration light source prior to returning the light from the retina of the eye through the variable focal length lens to the wavefront sensor to ascertain the at least one parameter of the variable focal length lens; and
subsequently switching off the calibration light source while returning the light from the retina of the eye through the variable focal length lens to a wavefront sensor.

21. The method of claim 16, wherein a wavelength of the probe light beam is different from a wavelength of the calibration light.

22. The method of claim 16, wherein the variable focal length lens comprises a liquid filled lens.

23. The method of claim 16, further comprising passing the probe light beam through the variable focal length lens to the eye, wherein the desired characteristic is a minimized spot size on the retina for the probe light beam.

24. The method of claim 15, wherein the desired characteristic is collimation of the light received by the wavefront sensor.

* * * * *